(12) United States Patent
Morley et al.

(10) Patent No.: US 11,964,001 B2
(45) Date of Patent: Apr. 23, 2024

(54) COMPOSITIONS FOR TREATING OR PREVENTING RESPIRATORY TRACT INFECTIONS AND METHOD OF USE THEREOF

(71) Applicants: Sharon Celeste Morley, St. Louis, MO (US); Elizabeth M. Todd, St. Louis, MO (US)

(72) Inventors: Sharon Celeste Morley, St. Louis, MO (US); Elizabeth M. Todd, St. Louis, MO (US)

(73) Assignee: Washington University, St. Louis, MO (US)

( * ) Notice: Subject to any disclaimer, the term of this patent is extended or adjusted under 35 U.S.C. 154(b) by 446 days.

(21) Appl. No.: 16/844,690

(22) Filed: Apr. 9, 2020

(65) Prior Publication Data

US 2020/0323959 A1   Oct. 15, 2020

Related U.S. Application Data

(60) Provisional application No. 62/831,318, filed on Apr. 9, 2019.

(51) Int. Cl.
*A61K 38/19* (2006.01)
*A61P 11/00* (2006.01)

(52) U.S. Cl.
CPC ............ *A61K 38/193* (2013.01); *A61P 11/00* (2018.01)

(58) Field of Classification Search
None
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,229,496 A | 7/1993 | Deeley et al. |
| 5,264,618 A | 11/1993 | Felgner et al. |
| 5,391,485 A | 2/1995 | Deeley et al. |
| 5,393,870 A | 2/1995 | Deeley et al. |
| 2015/0174204 A1* | 6/2015 | Heslet ..................... A61P 11/06 424/85.1 |

OTHER PUBLICATIONS

Guilliams et al. (2013, J. Exp. Med. 210(10):1977-1992).*
Prince et al. (2014, Plos One 9(8):1-12).*
Ballard et al. (2003, Am J Respir Crit Care Med 168:1123-1128).*
Griese (1999, Eur Respir J 13:1455-1476).*
Wright, J. et al., "Degradation of surfactant lipids and surfactant protein A by alveolar macrophages in vitro," Am. J. Physiol., 1995, pp. L772-L780, vol. 268.

Yona, S. et al., "Fate Mapping Reveals Origins and Dynamics of Monocytes and Tissue Macrophages under Homeostasis," Immunity, Jan. 24, 2013, pp. 79-91, vol. 38.
Yu, X. et al., "The Cytokine TGF-beta Promotes the Development and Homeostasis of Alveolar Macrophages," Immunity, Nov. 21, 2017, pp. 903-912, vol. 47.
Alenghat, E. et al., "Alveolar Macrophages in Perinatal Infants," Pediatrics, Aug. 1984, pp. 221-223, vol. 74, No. 2.
Altemeier, W. et al., "Hyperoxia in the intensive care unit: why more is not always better," Curr Opin Crit. Care, Feb. 2007, pp. 73-78, vol. 13, No. 1.
Andreeva, A. et al., "Regulation of surfactant secretion in alveolar type II cells," Am. J. Physiol. Lung Cell. Mol. Physiol., 2007, pp. L259-L271, vol. 293.
Baleeiro, C. et al., "GM-CSF and the impaired pulmonary innate immune response following hyperoxic stress," Am. J. Physiol. Lung Cell. Mol. Physiol., 2006, pp. L1246-L1255, vol. 291.
Bharat, A. et al., "Flow Cytometry Reveals Similarities Between Lung Macrophages in Humans and Mice," Am. J. Respir. Cell Mol. Biol., Jan. 2016, pp. 147-149, vol. 54, No. 1.
Blackwell, T. et al., "NF-kB Signaling in Fetal Lung Macrophages Disrupts Airway Morphogenesis," J. Immunol., 2011, pp. 2740-2747, vol. 187.
Bry, K. et al., "Granulocyte-Macrophage Colony-Stimulating Factor in Amniotic Fluid and in Airway Specimens of Newborn Infants," Pediatr. Res., Jan. 1997, pp. 105-109, vol. 41.
Burgess, A. et al., "Purification and Properties of Bacterially Synthesized Human Granulocyte-Macrophage Colony Stimulating Factor," Blood, 1987, pp. 43-51, vol. 69, No. 1.
Carr, R. et al., "Granulocyte-macrophage colony stimulating factor administered as prophylaxis for reduction of sepsis in extremely preterm, small for gestational age neonates (the Programs trial): a single-blind, multicentre, randomised controlled trial," Lancet, Jan. 2009, pp. 226-233, vol. 373, No. 9659.
Chen, G-H. et al., "Role of Granulocyte Macrophage Colony-Stimulating Factor in Host Defense Against Pulmonary Cryptococcus neoformans Infection during Murine Allergic Bronchopulmonary Mycosis," Am. J. Pathol., Mar. 2007, pp. 1028-1040, vol. 170, No. 3.
Deady, L. et al., "L-Plastin Is Essential for Alveolar Macrophage Production and Control of Pulmonary Pneumococcal Infection," Infect. Immun., May 2014, pp. 1982-1993, vol. 82, No. 5.
Dong, Q. et al., "Degradation of surfactant protein D by alveolar macrophages," Am. J. Physiol., 1998, pp. L97-L105, vol. 274.
Farver, C et al., "Lung Macrophage Differentiation in Developing Fetal and Newborn Rat Lungs: A Quantitative Flow Cytometric Analysis with Immunohistochemistry," Lung, 1999, pp. 205-217, vol. 177.
Gautier, E. et al., "Gata6 regulates aspartoacylase expression in resident peritoneal macrophages and controls their survival," J. Exp. Med., 2014, pp. 1525-1531, vol. 211, No. 8.

(Continued)

*Primary Examiner* — Elizabeth C. Kemmerer
(74) *Attorney, Agent, or Firm* — Polsinelli PC

(57) ABSTRACT

The present invention provides compositions and method for treating a subject having or suspected of having pulmonary dysfunction resulting from impaired alveolar macrophage (AM) development. The compositions comprise granulocyte-macrophage colony stimulating factor (GM-CSF) in formulations suitable for pulmonary airway administration.

**18 Claims, 21 Drawing Sheets
(3 of 21 Drawing Sheet(s) Filed in Color)
Specification includes a Sequence Listing.**

(56) References Cited

OTHER PUBLICATIONS

Gibbings, S. et al., "Three Unique Interstitial Macrophages in the Murine Lung at Steady State," Am. J. Respir. Cell Mol. Biol., Jul. 2017, pp. 66-76, vol. 57, No. 1.
Guilliams, M. et al., "Alveolar macrophages develop from fetal monocytes that differentiate into long-lived cells in the first week of life via GM-CSF," J. Exp. Med., 2013, pp. 1977-1992, vol. 210, No. 10.
Hashimoto, D. et al., "Tissue-Resident Macrophages Self-Maintain Locally throughout Adult Life with Minimal Contribution from Circulating Monocytes," Immunity, Apr. 18, 2013, pp. 792-804, vol. 38.
Herold, S. et al., "Inhales Granulocyte/Macrophage Colony-Stimulating Factor as Treatment of Pneumonia- associated Acute Respiratory Distress Syndrome," Am. J. Respir. Crit. Care Med., Mar. 1, 2014, pp. 609-611, vol. 189, No. 5.
Huang, F-F. et al., "GM-CSF in the Lung Protects against Lethal Influenza Infection," Am. J. Respir. Crit. Care Med., 2011, pp. 259-268, vol. 184.
Jakubzick, C. et al., "Monocyte differentiation and antigen-presenting functions," Nat. Rev. Immunol., Jun. 2017, pp. 349-362, vol. 17.
Kaushansky, K. et al., "Genomic cloning, characterization, and multilineage growth-promoting activity of human granulocyte-macrophage colony-stimulating factor," PNAS, May 1986, pp. 3101-3105, vol. 83.
Kopf, M. et al., "The development and function of lung-resident macrophages and dendritic cells," Nat. Immunol., Jan. 2015, pp. 1-9, vol. 16, No. 1.
Marlow, N. et al., "A randomised trial of granulocyte-macrophage colony-stimulating factor for neonatal sepsis: outcomes at 2 years," Arch. Dis. Child. Fetal Neonatal Ed., 2013, pp. F46-F53, vol. 98.
Marlow, N. et al., "A randomised trial of granulocyte-macrophage colony-stimulating factor for neonatal sepsis: childhood outcomes at 5 years," Arch. Dis. Child. Fetal Neonatal Ed., 2015, pp. F320-F326, vol. 100.
Mass, E. et al., "Specification of tissue-resident macrophages during organogenesis," Sci., 2016, pp. 1-26, vol. 353, aaf4238.
Mould, K. et al., "Cell Origin Dictates Programming of Resident versus Recruited Macrophages during Acute Lung Injury," Am. J. Respir. Cell Mol. Biol., Sep. 2017, pp. 294-306, vol. 57, No. 3.
O'Brien, K. et al., "Burden of disease caused by *Streptococcus pneumoniae* in children younger than 5 years: global estimates," Lancet, Sep. 2009, pp. 893-902, vol. 374, No. 9693.
Perdiguero, E. et al., "Tissue-resident macrophages originate from yolk-sac-derived erythro-myeloid progenitors," Nature, 2014, pp. 1-5, with Methods, 12 pgs.
Plantinga, M. et al., "Conventional and Monocyte-Derived CD11b+ Dendritic Cells Initiate and Maintain T Helper 2 Cell-Mediated Immunity in House Dust Mite Allergen," Immunity, Feb. 21, 2013, pp. 322-335, vol. 38.
Prince, L. et al., "Macrophage Phenotype Is Associated with Disease Severity in Preterm Infants with Chronic Lung Disease," Plos One, Aug. 2014, pp. 1-12, vol. 9, No. 8, e103059.
Pryhuber, G. et al., "Postnatal Infections and Immunology Affecting Chronic Lung Disease of Prematurity," Clin. Perinatol., 2015, pp. 697-718, vol. 42.
Puljic, R. et al., "Lipopolysaccharide-induced lung inflammation is inhibited by neutralization of GM-CSF," Eur. J. Pharmacol., 2007, pp. 230-235, vol. 557, Nos. 2-3.
Schneider, C. et al., "Induction of the nuclear receptor PPAR-γ by the cytokine GM-CSF is critical for the differentiation of fetal monocytes into alveolar macrophages," Nat. Immunol., 2014, pp. 1-12, vol. 15.
Schneider, C. et al., "Alveolar Macrophages Are Essential for Protection from Respiratory Failure and Associated Morbidity following Influenza Virus Infection," Plos Pathog., Apr. 2014, pp. 1-15, vol. 10, No. 4, e1004053.
Schulz, C. et al., "A Lineage of Myeloid Cells Independent of Myb and Hematopoietic Stem Cells," Sci., Apr. 6, 2013, pp. 86-90, vol. 336.
Scott, J. et al., "Inhaled granulocyte-macrophage colony-stimulating factor for *Mycobacterium* abscesses in cystic fibrosis," Eur. Respir. J., 2018, pp. 1-3, vol. 51, 1702127.
Sheng, G. et al., "Better approach for autoimmune pulmonary alveolar proteinosis treatment: inhaled or subcutaneous granulocyte-macrophage colony-stimulating factor: a meta-analyses," Respir. Res., 2018, pp. 1-11, vol. 163.
Sherman, M. et al., "Role of Pulmonary Phagocytes in Host Defense against Group B Steptococci in Preterm versus Term Rabbit Lung," J. Infect. Dis., Oct. 1992, pp. 818-826, vol. 166, No. 4.
Steinwede, K. et al., "Local Delivery of GM-CSF Protects Mice from Lethal Pneumococcal Pneumonia," J. Immunol., Oct. 2011, pp. 5346-5356, vol. 187.
Studier, W., "Protein production by auto-induction in high-density shaking cultures," Protein Expr. Purif., 2005, pp. 207-234, vol. 41.
Suzuki, T. et al., "Pulmonary Macrophage Transplantation Therapy," HHS Public Access Author Manuscript, Apr. 23, 2015, pp. 1-37, published in final edited form as: Nature, Oct. 23, 2014, pp. 450-454, vol. 514, No. 7523.
Todd, E. et al., "The Actin Bundling Protein L-Plastin Is Essential for Marginal Zone B Cell Development," J. Immunol., 2011, pp. 3015-3025, vol. 187.
Todd, E. et al., "Alveolar macrophage development in mice requires L-plastin for cellular localization in alveoli," Blood, Dec. 15, 2016, pp. 2785-2796, vol. 128, No. 24.
Todd, E. et al., "Inhaled GM-CSF in neonatal mice provides durable protection against bacterial pneumonia," Sci. Adv., 2019, p. 1-9, vol. 5, eaax3387.
Trapnell, B. et al., "GM-CSF Regulates Pulmonary Surfactant Homeostatis and Alveolar Macrophage-Mediated Innate Host Defense," Annu. Rev. Physiol., 2002, pp. 775-802, vol. 64.
Trapnell, B. et al., "Pulmonary alveolar proteinosis, a primary immunodeficiency of impaired GM-CSF stimulation of macrophages," NIH Public Access Author Manuscript, Oct. 1, 2010, pp. 1-15, published in final edited form as: Curr. Opin. Immunol., Oct. 2009, pp. 514-521, vol. 21, No. 5.
Van De Laar, L. et al., "Yolk Sac Macrophages, Fetal Liver, and Adult Monocytes Can Colonize an Empty Niche and Develop into Functional Tissue-Resident Macrophages," Immunity, 2016, pp. 755-768, vol. 44.
Whitsett, J. et al., "Alveolar Development and Disease," Am. J. Respir. Cell Mol. Biol., Jul. 2015, pp. 1-7, vol. 53, No. 1.
Wong, G. et al., "Human GM-CSF: Molecular Cloning of the Complementary DNA and Purification of the Natural and Recombinant Proteins," Sci., May 17, 1985, pp. 810-815, vol. 228, No. 4701.

* cited by examiner

SEQUENCE LISTING

```
<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Gly Met Cys Ser Phe Met Ala Pro Ala Arg Ser Pro Ser Pro Ser Thr
1               5                   10                  15

Gln Pro Trp Glu His Val Asn Ala Ile Gln Glu Ala Arg Arg Leu Leu
            20                  25                  30

Asn Leu Ser Arg Asp Thr Ala Ala Glu Met Asn Glu Thr Val Glu Val
        35                  40                  45

Ile Ser Glu Met Phe Asp Leu Gln Glu Pro Thr Cys Leu Gln Thr Arg
    50                  55                  60

Leu Glu Leu Tyr Lys Gln Gly Leu Arg Gly Ser Leu Thr Lys Leu Lys
65                  70                  75                  80

Gly Pro Leu Thr Met Met Ala Ser His Tyr Lys Gln His Cys Pro Pro
            85                  90                  95

Thr Pro Glu Thr Ser Cys Ala Thr Gln Ile Ile Thr Phe Glu Ser Phe
            100                 105                 110

Lys Glu Asn Leu Lys Asp Phe Leu Leu Val Ile Pro Phe Asp Cys Trp
            115                 120                 125

Glu Pro Val Gln Glu
            130
```

COMPOSITIONS FOR TREATING OR PREVENTING RESPIRATORY TRACT INFECTIONS AND METHOD OF USE THEREOF

CROSS REFERENCE TO RELATED APPLICATIONS

This application claims the benefit of U.S. Provisional Application number 62/831,318 filed Apr. 9, 2019, the disclosure of which is hereby incorporated by reference in its entirety.

GOVERNMENTAL RIGHTS

This invention was made with government support under AI104732 awarded by the National Institutes of Health. The government has certain rights in the invention.

FIELD OF THE TECHNOLOGY

The present technology provides, in part, a method of treating a subject having or suspected of having pulmonary dysfunction resulting from impaired alveolar macrophage (AM) development by administering to the subject an effective amount of granulocyte-macrophage colony stimulating factor (GM-CSF) via pulmonary airway administration. In addition, the present technology also provide protection against respiratory infection in a subject having or suspected of having impaired alveolar macrophage (AM) development by administering to the subject an effective amount of granulocyte-macrophage colony stimulating factor (GM-CSF) via pulmonary airway administration.

BACKGROUND

The United Nations Children's Fund (UNICEF) estimates that pediatric pneumonia kills 3 million children worldwide each year. These deaths occur almost exclusively in children with underlying conditions, such as chronic lung disease of prematurity, congenital heart disease, and immunosuppression. Although most fatalities occur in developing countries, pneumonia remains a significant cause of morbidity in industrialized nations.

Newborns with pneumonia commonly present with poor feeding and irritability, as well as tachypnea, retractions, grunting, and hypoxemia. Infections with group B *Streptococcus, Listeria monocytogenes*, or gram-negative rods (e.g, *Escherichia coli, Klebsiella pneumoniae*) are common causes of bacterial pneumonia. Group B streptococci infections are most often transmitted to the fetus in utero. The most commonly isolated virus is respiratory syncytial virus (RSV).

Cough is the most common symptom of pneumonia in infants, along with tachypnea, retractions, and hypoxemia. These may be accompanied by congestion, fever, irritability, and decreased feeding. *Streptococcus pneumoniae* is by far the most common bacterial pathogen in infants aged 1-3 months. Adolescents experience similar symptoms to younger children. They may have other constitutional symptoms, such as headache, pleuritic chest pain, and vague abdominal pain. Vomiting, diarrhea, pharyngitis, and otalgia/otitis are also common in this age group. Mycoplasma pneumoniae is the most frequent cause of pneumonia among older children and adolescents.

Pneumonia causes considerable morbidity and mortality in premature infants and neonates (K. L. O'Brien et al., Lancet 374,893-902 (2009), G. S. Pryhuber et al., Clin. Perinatol. 42,697-718 (2015)), yet remarkably little is known about host susceptibility to, and the pathophysiology of, lower respiratory tract infections in this age group.

Accordingly, a need exist in the art for composition and methods to aid in the treatment and prevention of respiratory infections in premature infants and neonates.

SUMMARY

One aspect of the present disclosure provides a method for method of decreasing susceptibility to a respiratory tract infection in a subject having or suspected of having pulmonary dysfunction resulting from impaired alveolar macrophage development, the method comprising, administering to the subject an effective amount of granulocyte-macrophage colony stimulating factor (GM-CSF) or a functional homologue thereof via pulmonary airway administration. In one aspect, the subject is a preterm neonate. In some embodiments, the GM-CSF or a functional homologue thereof is administered at birth or shortly thereafter. In some embodiments, the susceptibility of infection in the subject is reduced relative to a subject with pulmonary dysfunction resulting from impaired AM development that has not been treated with GM-CSF or a functional homologue thereof. In some embodiments, the respiratory tract infection is bacterial pneumonia.

In some embodiments, shortly after birth is within about 1 minute, within about 2 minutes, within about 3 minutes, within about 4 minutes, within about 5 minutes, within about 10 minutes, within about 15 minutes, within about 20 minutes, within about 25 minutes, within about 30 minutes, within about 35 minutes, within about 40 minutes, within about 45 minutes, within about 50 minutes, within about 55 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours after birth.

In one aspect, the effective amount of GM-CSF or a functional homologue thereof is administered by intratracheal, intrabronchial or intraalveolar administration. In some embodiments, the subject is administered a nebulized aerosol, nebulized solution or inhaled powder form of GM-CSF or a functional homologue thereof.

In one aspect, the GM-CSF or functional homologue thereof is administered at birth and at least one time shortly thereafter.

Another aspect of the disclosure provides a method of treating a subject having or suspected of having pulmonary dysfunction resulting from impaired alveolar macrophage development, the method comprising, administering to the subject an effective amount of granulocyte-macrophage colony stimulating factor (GM-CSF) or a functional homologue thereof via pulmonary airway administration. In some embodiments, the subject is a preterm neonate. In one aspect, the GM-CSF or a functional homologue thereof is administered at birth or shortly thereafter. In one aspect, the GM-CSF or functional homologue thereof is administered at birth and at least one time shortly thereafter.

In some embodiments, shortly after birth is within about 1 minute, within about 2 minutes, within about 3 minutes, within about 4 minutes, within about 5 minutes, within about 10 minutes, within about 15 minutes, within about 20 minutes, within about 25 minutes, within about 30 minutes, within about 35 minutes, within about 40 minutes, within about 45 minutes, within about 50 minutes, within about 55 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours after birth.

In some embodiments, the effective amount of GM-CSF or a functional homologue thereof is administered by intratracheal, intrabronchial or intraalveolar administration. In one aspect, the subject is administered a nebulized aerosol, nebulized solution or inhaled powder form of GM-CSF or a functional homologue thereof.

In some embodiments, administration of GM-CSF or a functional homologue thereof results in increase alveolar macrophage or alveolar macrophage precursor proliferation. In some embodiments, administration of GM-CSF or a functional homologue thereof results improved lung surfactant homeostasis. In one aspect, improved lung surfactant homeostasis is measured by determining the levels of one or more of surfactant protein-D and surfactant protein-A. In another embodiment, the level of surfactant protein-D is reduced relative to a subject with pulmonary dysfunction resulting from impaired AM development.

BRIEF DESCRIPTION OF THE FIGURES

The application file contains at least one drawing executed in color. Copies of this patent application publication with color drawing(s) will be provided by the Office upon request and payment of the necessary fee.

FIG. 1A is a schematic showing rGM-CSF (20 ng) in 6 μl of PBS was administered via intranasal (i.n.) instillation to neonatal pups on DOB, PND1, and PND2. Mice were evaluated at indicated times after rGM-CSF administration. FIG. 1B shows representative flow cytometry of whole-lung homogenates from PND3 WT and $LPL^{-/-}$ pups treated intranasally with PBS or rGM-CSF. FIG. 1C shows the quantification of the distribution of monocytes, pre-AMs, AMs, and total $CD11c^+$ (maturing) cells in PND3 WT and $LPL^{-/-}$ pups. FIG. 1D shows representative flow cytometry from BAL fluid obtained from adult WT and $LPL^{-/-}$ mice that had received neonatal rGM-CSF therapy. FIG. 1E shows the percentage and number of AMs recovered from BAL fluid from adult WT and $LPL^{-/-}$ mice that had received neonatal rGM-CSF treatment. For FIG. 1C and FIG. 1E n of each group is provided below x axes. Data were obtained from four independent cohorts of animals. P values are determined using the Mann-Whitney U test. Kruskal-Wallis test comparing four groups revealed P=0.0014 for AM % (top) and P=0.015 for AM numbers (bottom). The "n" of AM numbers (bottom) in some groups is lower than AM % (top) because cell numbers in one experiment were counted manually rather than by cytometer acquisition. Only cell counts obtained by the same method (cytometer acquisition) are included in data shown here.

FIG. 2A shows the Experimental design: Neonatal WT and $LPL^{-/-}$ pups were intranasally given 20 ng of rGM-CSF or PBS (control) on DOB, PND1, and PND2. After reaching adulthood, mice were challenged intratracheally (i.t.) with pneumococcus. FIG. 2B shows adult WT (gray) or $LPL^{-/-}$ (black) mice that had received neonatal rGM-CSF therapy (open symbols) or PBS (control; closed symbols) were infected intratracheally with pneumococcus and monitored for survival. Survival curves show data combined from three independent experiments (WT+PBS, n=19; WT+rGM-CSF, n=7; $LPL^{-/-}$+PBS, n=11; $LPL^{-/-}$+rGM-CSF, n=16) and were compared using Mantel-Cox log-rank test. FIG. 2C shows a quantitative blood culture obtained from adult mice 24 hours after intratracheal instillation of pneumococci. Comparison of all groups by one-way analysis of variance (ANOVA) (Kruskal-Wallis test), P=0.0007. FIG. 2D shows distribution of neutrophils [polymorphonuclear leukocytes (PMNs)], monocytes, and B cells in the peripheral blood of WT and $LPL^{-/-}$ mice challenged with pneumococcus. Mice had received neonatal rGM-CSF therapy (GM) or PBS (P; control). FIG. 2E shows number of AMs recovered from BAL fluid of WT or $LPL^{-/-}$ adult mice that survived 2 weeks after intratracheal pneumococcal infection. Grossly bloody BAL fluids were excluded from analysis (clotted). FIG. 2F shows the distribution of DCs, eosinophils, neutrophils (PMNs), and monocytes in whole-lung homogenates from uninfected adult WT and $LPL^{-/-}$ mice that had received neonatal rGM-CSF therapy or PBS (control). Percentages of total CD45+ cells are given. (C to F) Data are combined from three (C to E) or two (F) independent experiments. n of each group is given below x axes. P values of comparisons between two groups are determined using the Mann-Whitney U test.

FIG. 3A shows a representative flow cytometry of BrdU incorporation into AMs and precursors (monocytes and pre-AMs, defined as shown) in whole-lung homogenates from PND3 WT and LPL–/– pups receiving rGM-CSF therapy or PBS (control). Percentage of cells in each gate incorporating BrdU listed in the top right-hand corner. FIG. 3B shows the quantification of the percentage of monocytes, pre-AMs, or AMs incorporating BrdU in PND3 WT or LPL–/– pups receiving neonatal rGM-CSF therapy (gray symbols) or PBS (control; open symbols). Each symbol represents one animal. Data are combined from three independent experiments. Line shows median value. P values are determined using the Mann-Whitney U test. FIG. 3C shows the TGF-β concentration in whole-lung homogenates from PND3 WT and LPL–/– pups receiving neonatal rGM-CSF therapy (gray bars) or PBS (open bars). Line shows the median value. n of each group is listed below the x axis. Data are from two independent cohorts of animals.

FIG. 4A shows SP-D concentrations in whole-lung homogenates obtained from PND3 pups or adult WT or LPL–/– mice that had received neonatal rGM-CSF therapy (gray bars) or PBS (control; open bars).shows frequencies of microglia in relation to Aβ plaques shown as white squares. FIG. 4B shows SP-A concentrations in whole-lung homogenates obtained from PND3 pups or adult WT or $LPL^{-/-}$ mice that had received neonatal rGM-CSF therapy (gray bars) or PBS (control; open bars). Line shows the median value. P values are determined using the Mann-Whitney U test. n of each group is listed below x axes. Data are combined from two independent cohorts of animals.

FIG. 6A shows lungs obtained from PND3 animals and sections were stained with hematoxylin and eosin. Sections were reviewed in a blinded fashion by a veterinary pathologist. Scale bars=100 µM. FIG. 6B shows lungs obtained from adult animals and sections were stained with hematoxylin and eosin. Sections were reviewed in a blinded fashion by a veterinary pathologist. Scale bars=100 µM.

FIG. 7A shows SP-D concentrations (normalized to total protein in lysates of lung tissue) in WT and $LPL^{-/-}$ mice (PND3 pups or adult) after receiving i.n. neonatal therapy with rGM-CSF (GM; gray bars) or PBS (open bars). FIG. 7B shows SP-A concentrations (normalized to total protein in lysates of lung tissue) in WT and LPL-/- mice (PND3 pups or adult) after receiving i.n. neonatal therapy with rGM-CSF (GM; gray bars) or PBS (open bars). Line at median; p-value determined with Mann-Whitney; n of each group listed below x-axes; data combined from two independent cohorts of animals.

DETAILED DESCRIPTION

Figure 1A:
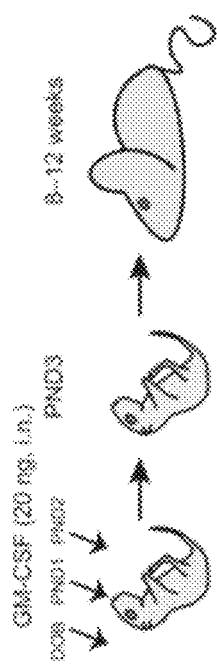
FIG. 1A, FIG. 1B, FIG. 1C, FIG. 1D, and FIG. 1E show administration for GM-CSF increases AMs in LPL –/– mice.

Pneumonia causes considerable morbidity and mortality in premature infants and neonates, yet remarkably little is known about host susceptibility to, and the pathophysiology of, lower respiratory tract infections in this age group. In particular, the development of innate immunity in preterm infant lungs is poorly understood. Given that alveolar macrophages (AMs) have unique roles as first responders to pathogenic infection and in maintaining the anti-inflammatory, homeostatic environment of the lungs conducive to appropriate lung development, understanding how the appearance of AMs is affected by preterm birth is essential to understanding how preterm infants may respond to pulmonary pathogen challenge.

A major paradigm shift occurred when Schulz et al. (C. Schulz et al., Science 336, 86-90 (2012)) demonstrated that tissue-resident macrophages arise during embryogenesis from yolk sac precursors and are not continuously rederived from circulating peripheral blood monocytes. The recognition that each tissue-resident macrophage lineage derives along a unique pathway, following distinct development and tissue-specific cues and finishing with specialized phenotypic markers and functions, revolutionized basic immunologists' understanding and appreciation for the complex nature of the tissue-resident phagocytic system (M. Guilliams et al., J. Exp. Med. 210, 1977-1992 (2013); M. Plantinga et al., Immunity 38, 322-335 (2013); S. Yona et al., Immunity 38, 79-91 (2013) E. L. Gautier et al., J. Exp. Med. 211, 1525-1531 (2014); C. Schneider et al., PLOS Pathog. 10, e1004053 (2014); C. Schneider et al., Nat. Immunol. 15, 1026-1037 (2014); E. Gomez Perdiguero et al., Nature 518, 547-551 (2015); M. Kopf et al., Nat. Immunol. 16, 36-44 (2015); E. Mass et al., Science 353, aaf4238 (2016); L. van de Laar et al., Immunity 44, 755-768 (2016); and C. V. Jakubzick et al., Nat. Rev. Immunol. 17, 349-362 (2017)).

AMs epitomize the highly specialized nature of tissue-resident macrophages, as they express CD11c (not CD11b) and depend on the growth factor granulocyte-macrophage colony-stimulating factor (GM-CSF) and the transcription factor peroxisome proliferator-activated receptor γ. They also arise during a temporally limited phase of development, which in mice begins on embryonic day 16 and closes on postnatal day 7 (PND7). They arise from monocyte precursor cells that seed the lungs of mice during embryonic days 15 and 16, coincident with the saccular phase of lung development (J. A. Whitsett et al., Am. J. Respir. Cell Mol. Biol. 53,1-7 (2015)). These monocytes develop to the intermediary pre-AM in the days before birth and then advance to fully mature AMs in mice by PND7 (M. Guilliams et al., J. Exp. Med. 210,1977-1992 (2013)). Pre-AMs and AMs are phenotypically distinguished by surface markers; pre-AMs express CD11c, while AMs express both CD11c and SiglecF. The pre-AM, as a developmental intermediary, can only be found in the lungs from late embryonic or early neonatal mice (not adult). AM development during the perinatal period is driven by a burst of GM-CSF production, which subsides after birth (C. Schneider et al., Nat. Immunol. 15,1026-1037 (2014)). After the first week of life, no new precursor cells are generated, and in the absence of overwhelming inflammation, AMs self-renew over the lifetime of the host (M. Guilliams et al., J. Exp. Med. 210, 1977-1992 (2013), D. Hashimoto et al., Immunity 38,792-804 (2013)).

In addition to serving as sentinel cells, engulfing pathogens, and preventing subsequent lung infection (C. Schneider et al., PLOS Pathog. 10, e1004053 (2014), E. M. Todd et al., Blood 128,2785-2796 (2016)), AMs are functionally distinct from interstitial lung macrophages in that AMs are programmed to tilt toward an anti-inflammatory, prohealing phenotype. AMs thus protect and preserve the delicate alveolar structure from inflammatory insults. In human infants, AMs can arise post-natally in the first 2 days (E. Alenghat et al., Pediatrics 74,221-223 (1984), M. P. Sherman et al., J. Infect. Dis. 166,818-826 (1992), L. R. Prince et al., PLOS ONE 9, e103059 (2014), K. Bry et al., Pediatr. Res. 41,105-109 (1997), A. Bharat et al., Am. J. Respir. Cell Mol. Biol. 54,147-149 (2016)); therefore, the present disclosure provides that the exogenous augmentation of AM development represents a new avenue to protect preterm infants from pulmonary disease.

As shown herein, using a mouse model featuring the partial disruption of AM development, the compositions and methods of the disclosure provide sustained protection against respiratory tract infection in susceptible neonatal subjects, without perturbing airway immunity and lung development in the normal host, which illuminates how the airway administration of GM-CSF can be used in preterm infants to improve clinical outcomes in this highly vulnerable patient population. The muse model of disrupted AM development renders the mice susceptible to pneumococcal challenge (E. M. Todd et al., Blood 128,2785-2796 (2016), L. E. Deady et al., Infect. Immun. 82, 1982-1993 (2014)). Mice lacking the actin-bundling protein L-plastin ($LPL^{-/-}$ mice) and $CD11c.Cre^+-LPL^{fl/fl}$ mice exhibited cell intrinsic defects in AM production secondary to the diminished migration of AM precursors to, and retention within, the alveoli. $LPL^{-/-}$ and $CD11c.Cre^+-LPL^{fl/fl}$ mice also exhibited impaired pneumococcal clearance from the lungs following intratracheal challenge, associated with increased dissemination to the bloodstream and decreased survival (E. M. Todd et al., Blood 128,2785-2796 (2016), L. E. Deady et al., Infect. Immun. 82,1982-1993 (2014)). Because GM-CSF signaling is independent of LPL (. M. Todd et al., Blood 128,2785-2796 (2016)), it is considered that these mice to represent an ideal model system to test the therapeutic potential of GM-CSF delivery to neonates. As provided herein intranasal administration of GM-CSF to neonatal mice in the first week of life enhances AM development. Importantly, systemic administration of GM-CSF did not enhance AM maturation as did direct airway administration, and therefore, these effects would not have been apparent in prior clinical trials of GM-CSF in preterm infants (R. Carr et al., Lancet 373,226-233 (2009)). Most notably, the augmented population of AMs persists to adulthood, and animals treated in the neonatal period are protected as adults from mortality during pneumococcal lung infection.

Accordingly, the present disclosure provides compositions comprising granulocyte-macrophage colony stimulating factor (GM-CSF), or a functional homologue of thereof, suitable for intratracheal, intrabronchial or bronchio-alveolar administration, by any appropriate method including, but not limited to, intratracheal, intrabronchial or intraalveolar administration. The present disclosure also provides a method of treating a subject having or suspected of having pulmonary dysfunction resulting from impaired alveolar macrophage development by administering to the subject an effective amount of granulocyte-macrophage colony stimulating factor (GM-CSF) via pulmonary airway administration. In another aspect, the present disclosure provides protection against respiratory tract infections in a subject having or suspected of having impaired alveolar macrophage development by administering to the subject an effective amount of granulocyte-macrophage colony stimulating factor (GM-CSF) via pulmonary airway administration. In another aspect, the disclosure provides a method of preventing chronic lung disease, or broncho pulmonary dysplasia in a subject suspected having or suspected of having pulmonary dysfunction resulting from impaired alveolar macrophage development comprising administering to the subject an effective amount of granulocyte-macrophage colony stimulating factor (GM-CSF) via pulmonary airway administration. In another aspect the present disclosure provides a method of improving lung surfactant homeostasis in a subject suspected having or suspected of having pulmonary dysfunction resulting from impaired alveolar macrophage development comprising administering to the subject an effective amount of granulocyte-macrophage colony stimulating factor (GM-CSF) via pulmonary airway administration. In still another aspect, the present disclosure provides a method of increasing alveolar macrophage or alveolar macrophage precursor numbers in a subject having or suspected of having pulmonary dysfunction resulting from impaired alveolar macrophage development comprising administering to the subject an effective amount of granulocyte-macrophage colony stimulating factor (GM-CSF) via pulmonary airway administration.

Additional aspects of the disclosure are described below.

I. COMPOSITIONS

One aspect of the present disclosure encompasses compositions comprising GM-CSF. Colony-stimulating factors are glycoproteins that stimulate the growth of hematopoietic progenitors and enhance the functional activity of mature effector cells. In brief, at the level of immature cells, CSF's assure the self-renewal of the staminal pool and activate the first stage of hematopoietic differentiation; in the middle stage, when cell proliferation is associated to a progressive acquisition of characteristics of mature cells, they enormously enhance the number of differentiating cells; in the terminal stage they control the circulation and the activation of mature cells.

Mature GM-CSF is a monomeric protein of 127 amino acids with several potential glycosylation sites. The variable degree of glycosylation results in a molecular weight range between 14 kDa and 35 kDa. Non-glycosylated and glycosylated GM-CSF show similar activity in vitro. The crystallographic analysis of GM-CSF revealed a barrel-shaped structure composed of four short alpha helices. There are two known sequence variants of GM-CSF.

GM-CSF exerts its biological activity by binding to its receptor. The most important sites of GM-CSF receptor (GM-CSF-R) expression are on the cell surface of myeloid cells, such as alveolar macrophages type I & II, epithelial pulmonary cells and endothelial cells, whereas lymphocytes are GM-CSF-R negative. The native receptor is composed of at least two subunits, alpha and beta. The alpha subunit imparts ligand specificity and binds GM-CSF with nanomolar affinity. The beta subunit is also part of the interleukin-3 and interleukin-5 receptor complexes and, in association with the GM-CSF receptor alpha subunit and GM-CSF, leads to the formation of a complex with picomolar binding affinity. The binding domains on GM-CSF for the receptor have been mapped: GM-CSF interacts with the beta subunit of its receptor via a very restricted region in the first alpha helix of GM-CSF. Binding to the alpha subunit could be mapped to the third alpha helix, helix C, the initial residues of the loop joining helices C and D, and to the carboxyterminal tail of GM-CSF.

Formation of the GM-CSF trimeric receptor complex leads to the activation of complex signaling cascades involving molecules of the JAK/STAT families, She, Ras, Raf, the MAP kinases, phosphatidylinositol-3-kinase and NFkB, finally leading to transcription of c-myc, c-fos and c-jun. Activation is mainly induced by the beta subunit of the receptor. The shared beta subunit is also responsible for the overlapping functions exerted by IL-3, IL-5 and GM-CSF.

Apart from its hemopoietic growth and differentiation stimulating activity, GM-CSF functions especially as a proinflammatory cytokine. Macrophages, e.g. alveolar macrophages type I & II and monocytes as well as neutrophils and eosinophils become activated by GM-CSF, resulting in the release of other cytokines and chemokines, matrix degrading proteases, increased HLA expression and increased expression of cell adhesion molecules or receptors for CC-chemokines which in turn, leads to increased chemotaxis of inflammatory cells into inflamed tissue.

Wong et al., Science Vol. 228, pp. 810-815 (1985) and Kaushansky et al., Proc. Natl. Acad. Sci. USA, Vol. 83, pp. 3101-3105 (1986) have described the production of recombinant GM-CSF in mammalian cells. Burgess et al., Blood, Vol. 69, pp. 43-51 (1987) describes the purification of GM-CSF produced in *Escherichia coli*.

GM-CSF can be a recombinant granulocyte-macrophage colony-stimulating factor (GM-CSF) or a pharmaceutical analog of GM-CSF (e.g., sargramostim, molgramostim). GM-CSF is also known as colony-stimulating factor 2 (CSF2). A functional homologue of GM-CSF is a polypeptide having at least 50% sequence identity with SEQ ID NO. 1 and has one or more GM-CSF functions, such as the stimulation of the proliferation of alveolar macrophages and/or alveolar macrophage precursor cells or improvement of lung surfactant homeostasis.

GM-CSF regulates multiple functions of alveolar macrophages (AM). GM-CSF stimulation of AM has been documented to enhance alveolar macrophages selectively respond to noxious ingestants, i.e., stimulation of inflammation during bacterial phagocytosis, nonnoxious ingestants are generally mollified, i.e., anti-inflammatory responses during phagocytosis of apoptotic cells. Further AM functions are enhanced by GM-CSF stimulation with subsequent proliferation, differentiation, accumulation and activation. Further these GM-CSF effects also encompasses cell adhesion, improved chemotaxis, Fc-receptor expression, complement- and antibody-mediated phagocytosis, oxidative metabolism, intracellular killing of bacteria, fungi, protozoa, and viruses, cytokine signaling, and antigen presentation. Further GM-CSF enhances defects in AM cell adhesion, pathogen associated molecular pattern receptors, like Toll-like receptors and TLR trans-membranous signaling, surfactant protein and lipid uptake and degradation (Trapnell B C and Whitsett J A. Annu. Rev. Physiol. 64:775-802 (2002)).

Further GM-CSF interacts with the AM's recognition receptors, the so-called toll like receptors (TLR). GM-CSF is important in the pulmonary host defense in pneumonia due to its interaction with the TLR's participation in the host defense resulting in enhanced clearance of the causative microorganism (Chen G H et al., Am J Pathol.; 170(3):1028-40 (2007)). Lung has its own innate GM-CSF production, which is reduced in pneumonia and hyperoxia, in relation to high $O_2$ exposure as seen in, e.g. ventilator associated pneumonia (VAP) contributing impairment of host defense secondary to apoptosis with poor response to infections. The hyperoxic injury seems to be counteracted by activation of alveolar macrophages with GM-CSF (Altemeier W A et al., Curr Opin Crit. Care.; 13(1):73-8 (2007); Baleeiro C E et al., Am J Physiol Lung Cell Mol Physiol.; 291 (6):L1246-55 (2006) with subsequent clearance of *P. aeruginosa* via expression of the TLR signaling pathway (Baleeiro C E et al., Am J Physiol Lung Cell Mol Physiol. 291 (6):L1246-55 (2006)).

A functional GM-CSF homologue can be an evolutionary conservation between GM-CSF of different closely related species, e.g. assessed by sequence alignment, can be used to pinpoint the degree of evolutionary pressure on individual residues. Preferably, GM-CSF sequences are compared between species where GM-CSF function is conserved, for example but not limited to mammals including rodents, monkeys and apes. Residues under high selective pressure are more likely to represent essential amino acids that cannot easily be substituted than residues that change between species. It is evident from the above that a reasonable number of modifications or alterations of the human GM-CSF sequence does not interfere with the activity of the GM-CSF molecule according to the invention. Such GM-CSF molecules are herein referred to as functional equivalents of human GM-CSF, and may be such as variants and fragments of native human GM-CSF as described here below.

As used herein the expression "variant" refers to polypeptides or proteins which are homologous to the basic protein, which is suitably human GM-CSF, but which differs from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide.

A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterized by having i) polar side chains (Asp, Glu, Lys, Arg, His, Asn, Gln, Ser, Thr, Tyr, and Cys,)
ii) non-polar side chains (Gly, Ala, Val, Leu, Ile, Phe, Trp, Pro, and Met)
iii) aliphatic side chains (Gly, Ala Val, Leu, Ile)
iv) cyclic side chains (Phe, Tyr, Trp, His, Pro)
v) aromatic side chains (Phe, Tyr, Trp)
vi) acidic side chains (Asp, Glu)
vii) basic side chains (Lys, Arg, His)
viii) amide side chains (Asn, Gln)
ix) hydroxy side chains (Ser, Thr)
x) sulphur-containing side chains (Cys, Met), and
xi) amino acids being monoamino-dicarboxylic acids or monoamino-monocarboxylic-monoamidocarboxylic acids (Asp, Glu, Asn, Gln).

A functional homologue within the scope of the present invention is a polypeptide that exhibits at least 50% sequence identity with human GM-CSF as identified by SEQ ID NO. 1, preferably at least 60%, 70% sequence identity preferably functional homologues have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with SEQ ID NO: 1.

Sequence identity can be calculated using a number of well-known algorithms and applying a number of different gap penalties. Any sequence alignment algorithm, such as but not limited to FASTA, BLAST, or GETSEQ may be used for searching homologues and calculating sequence identity. Moreover, when appropriate any commonly known substitution matrix, such as but not limited to PAM, BLOSSUM or PSSM matrices, may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

Aside from the twenty standard amino acids and two special amino acids, selenocysteine and pyrrolysine, there are a vast number of "nonstandard amino acids" which are not incorporated into protein in vivo. Examples of nonstandard amino acids include the sulfur-containing taurine and the neurotransmitters GABA and dopamine. Other examples are lanthionine, 2-Aminoisobutyric acid, and dehydroalanine. Further non standard amino are ornithine and citrulline.

Non-standard amino acids are usually formed through modifications to standard amino acids. For example, taurine can be formed by the decarboxylation of cysteine, while dopamine is synthesized from tyrosine and hydroxyproline is made by a posttranslational modification of proline (common in collagen). Examples of non-natural amino acids are those listed e.g. in 37 C.F.R. section 1.822(b)(4), all of which are incorporated herein by reference.

Both standard and non standard amino acid residues described herein can be in the "D" or "L" isomeric form.

It is contemplated that a functional equivalent according to the invention may comprise any amino acid including non-standard amino acids. In preferred embodiments a functional equivalent comprises only standard amino acids. A functional equivalent can be determined, for example, using the methods disclosed in the Examples below.

The standard and/or non-standard amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Suitably variants will be at least 60% identical, preferably at least 70% and accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence of human GM-CSF.

Functional equivalents may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in fragment including at any one or both of the N- and C-termini, by means known in the art.

The term "fragment thereof" may refer to any portion of the given amino acid sequence. Fragments may comprise more than one portion from within the full-length protein, joined together. Suitable fragments may be deletion or addition mutants. The addition of at least one amino acid may be an addition of from preferably 2 to 250 amino acids, such as from 10 to 20 amino acids, for example from 20 to 30 amino acids, such as from 40 to 50 amino acids. Fragments may include small regions from the protein or combinations of these.

Suitable fragments may be deletion or addition mutants. The addition or deletion of at least one amino acid may be an addition or deletion of from preferably 2 to 250 amino acids, such as from 10 to 20 amino acids, for example from 20 to 30 amino acids, such as from 40 to 50 amino acids. The deletion and/or the addition may—independently of one another—be a deletion and/or an addition within a sequence and/or at the end of a sequence.

Deletion mutants suitably comprise at least 20 or 40 consecutive amino acid and more preferably at least 80 or 100 consecutive amino acids in length. Accordingly such a fragment may be a shorter sequence of the sequence as identified by SEQ ID NO: 1 comprising at least 20 consecutive amino acids, for example at least 30 consecutive amino acids, such as at least 40 consecutive amino acids, for example at least 50 consecutive amino acids, such as at least 60 consecutive amino acids, for example at least 70 consecutive amino acids, such as at least 80 consecutive amino acids, for example at least 90 consecutive amino acids, such as at least 95 consecutive amino acids, such as at least 100 consecutive amino acids, such as at least 105 amino acids, for example at least 110 consecutive amino acids, such as at least 115 consecutive amino acids, for example at least 120 consecutive amino acids, wherein said deletion mutants preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with SEQ ID NO: 1.

It is preferred that functional homologues of GM-CSF comprises at the most 500, more preferably at the most 400, even more preferably at the most 300, yet more preferably at the most 200, such as at the most 175, for example at the most 160, such as at the most 150 amino acids, for example at the most 144 amino acids.

The term "fragment thereof" may refer to any portion of the given amino acid sequence. Fragments may comprise more than one portion from within the full-length protein, joined together. Portions will suitably comprise at least 5 and preferably at least 10 consecutive amino acids from the basic sequence. They may include small regions from the protein or combinations of these.

There are two known variants of human GM-CSF; a T115I substitution in variant and a I117T substitution in variant 2. Accordingly, in one embodiment of the invention functional homologues of GM-CSF comprises a sequence with high sequence identity to SEQ ID NO: 1 or any of the splice variants.

Analogs of GM-CSF are for example described in U.S. Pat. Nos. 5,229,496, 5,393,870, and 5,391,485 to Deeley, et al. Such analogues are also functional equivalents comprised within the present disclosure.

The present disclosure relates to the pulmonary administration, of granulocyte-macrophage colony stimulating factor (GM-CSF), or a functional homologue of thereof, however prepared, to enhance the pulmonary host defense. GM-CSF can be produced in various ways, such as isolation from for example human or animal serum or from expression in cells, such as prokaryotic cells, yeast cells, insect cells, mammalian cells or in cell-free systems.

In one embodiment, GM-CSF is produced recombinantly by host cells. Thus, in one aspect, GM-CSF is produced by host cells comprising a first nucleic acid sequence encoding the GM-CSF operably associated with a second nucleic acid capable of directing expression in said host cells. The second nucleic acid sequence may thus comprise or even consist of a promoter that will direct the expression of protein of interest in said cells. A skilled person will be readily capable of identifying useful second nucleic acid sequence for use in a given host cell.

The process of producing recombinant GM-CSF in general comprises the steps of: providing a host cell, preparing a gene expression construct comprising a first nucleic acid encoding GM-CSF operably linked to a second nucleic acid capable of directing expression of said protein of interest in the host cell, transforming the host cell with the construct, cultivating the host cell, thereby obtaining expression of GM-CSF.

The recombinant GM-CSF thus produced may be isolated by any conventional method, such as any of the methods for protein isolation described herein below. The skilled person will be able to identify a suitable protein isolation steps for purifying GM-CSF.

In one embodiment of the invention, the recombinantly produced GM-CSF is excreted by the host cells. When GM-CSF is excreted the process of producing a recombinant protein of interest may comprise the following steps, providing a host cell, preparing a gene expression construct comprising a first nucleic acid encoding GM-CSF operably linked to a second nucleic acid capable of directing expression of said protein of interest in said host cell, transforming said host cell with the construct, cultivating the host cell, thereby obtaining expression of GM-CSF and secretion of GM-CSF into the culture medium, thereby obtaining culture medium comprising GM-CSF.

The composition comprising GM-CSF and nucleic acids may thus in this embodiment, comprise the culture medium or a composition prepared from the culture medium.

In another embodiment, said composition is an extract prepared from animals, parts thereof or cells or an isolated fraction of such an extract.

In an embodiment, GM-CSF is recombinantly produced in vitro in host cells and is isolated from cell lysate, cell extract or from tissue culture supernatant. In a more preferred embodiment GM-CSF is produced by host cells that are modified in such a way that they express GM-CSF. In an even more preferred embodiment of the invention said host cells are transformed to produce and excrete GM-CSF.

Dosages of a granulocyte-macrophage colony stimulating factor (GM-CSF), or a functional homologue of thereof can vary between wide limits, depending upon the disease or disorder to be treated, the age and condition of the subject to be treated. In general, the granulocyte-macrophage colony stimulating factor (GM-CSF), or a functional homologue of thereof is administered in a therapeutically effective amount. An "effective amount" as used is meant a dose, which, when administered via pulmonary administration, achieves a concentration in the subject's airways and/or lung parenchyma which increases the number or proliferation of AM, AM precursors, improves lung surfactant homeostasis, decreases the susceptibility to infection, and/or provides sustained protection against respiratory infection. In an embodiment where the composition comprising granulocyte-macrophage colony stimulating factor (GM-CSF), or a functional homologue of thereof is administered to a subject, the dose of a granulocyte-macrophage colony stimulating factor (GM-CSF), or a functional homologue of thereof may be from about 0.1 µg to about 10000 µg active ingredient per ml solution. For example, the dose of a granulocyte-macrophage colony stimulating factor (GM-CSF), or a functional homologue of thereof may be about 0.1 µg/ml, about 0.5 µg/ml, about 1 µg/ml, about 5 µg/ml, about 10 µg/ml, about 15 µg/ml, about 20 µg/ml, about 25 µg/ml. Alternatively, the dose of a granulocyte-macrophage colony stimulating factor (GM-CSF), or a functional homologue of thereof may be about 25 µg/ml, about 50 µg/ml, about 75 µg/ml, about 100 µg/ml, about 125 µg/ml, about 150 mg/kg, about 175 µg/ml, about 200 µg/ml, about 225 µg/ml, or about 250 µg/ml. Additionally, the dose of a granulocyte-macrophage colony stimulating factor (GM-CSF), or a functional homologue of thereof may be about 300 µg/ml, about 325 µg/ml, about 350 µg/ml, about 375 µg/ml, about 400 µg/ml, about 425 µg/ml, about 450 µg/ml, about 475 µg/ml or about 500 µg/ml. Alternatively, the dose of a granulocyte-macrophage colony stimulating factor (GM-CSF), or a functional homologue of thereof may be about 750 µg/ml, about 1000 µg/ml, about 1250 µg/ml, about 1500 µg/ml, about 1750 µg/ml, about 2000 mg/kg, about 2250 µg/ml, about 2500 µg/ml, about 2750 µg/ml, or about 3000 µg/ml. Additionally, the dose of a granulocyte-macrophage colony stimulating factor (GM-CSF), or a functional homologue of thereof may be about 3250 µg/ml, about 3750 µg/ml, about 4000 µg/ml, about 4500 µg/ml, about 5000 µg/ml, about 6000 µg/ml, about 7000 µg/ml, about 8000 µg/ml, about 9000 ug/ml or about 10000 µg/ml.

A composition of the invention may optionally comprise one or more additional drug or therapeutically active agent in addition to the granulocyte-macrophage colony stimulating factor (GM-CSF), or a functional homologue of thereof disclosed herein. In some embodiments, the additional drug or therapeutically active agent may be, in non-limiting examples, an antibiotic agent, an anti-viral agent, an anti-inflammatory agent or a steroid. In some embodiments, an additional therapeutically active agent includes surfactant therapy. Administration of exogenous surfactant is the established treatment. In one aspect, early or "prophylactic" administration of surfactant is in combination with a GM-CSF composition.

Dosages of an additional drug or therapeutically active agent can vary between wide limits, depending upon the disease or disorder to be treated, the age and condition of the subject to be treated. In an embodiment where the composition further comprising at least one additional drug or therapeutically active agent is contacted with a sample, the concentration of the at least one additional drug or therapeutically active agent may be from about 0.01 µM to about 10 µM. Alternatively, the concentration of the at least one additional drug or therapeutically active agent may be from about 0.01 µM to about 5 µM. For example, the concentration of the at least one additional drug or therapeutically active agent may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, or about 10 µM. Additionally, the concentration of the at least one additional drug or therapeutically active agent be greater than 10 µM.

The present disclosure also provides pharmaceutical compositions. The pharmaceutical composition comprises a granulocyte-macrophage colony stimulating factor (GM-CSF), or a functional homologue of thereof disclosed herein, as an active ingredient, and at least one pharmaceutically acceptable excipient.

The pharmaceutically acceptable excipient may be a diluent, a buffering agent, a pH modifying agent, a disintegrant, a dispersant, a preservative, or a lubricant. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(iii) pH Modifier

In various embodiments, the excipient may be a pH modifier. By way of non-limiting example, the pH modifying agent may be sodium carbonate, sodium bicarbonate, sodium citrate, citric acid, or phosphoric acid.

(iv) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(v) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(vi) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(vii) Lubricant

In a further embodiment, the excipient may be a lubricant. Non-limiting examples of suitable lubricants include minerals such as talc or silica; and fats such as vegetable stearin, magnesium stearate, or stearic acid.

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered via pulmonary airway administration. Pulmonary airway administration includes intratracheal, intrabronchial or bronchio-alveolar administration such as, but limited to, spraying, lavage, inhalation, flushing or installation, using as fluid a physiologically acceptable composition in which GM-CSF have been dissolved. When used herein the terms "intratracheal, intrabronchial or intraalveolar administration" include all forms of such administration whereby GM-CSF is applied into the trachea, the bronchi or the alveoli, respectively, whether by the instillation of a solution of GM-CSF, by applying GM-CSF in a powder form, or by allowing GM-CSF to reach the relevant part of the airway by inhalation of GM-CSF as an aerosolized or nebulized solution or suspension or inhaled powder or gel, with or without added stabilizers or other excipients. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

Methods of intrabronchial/alveolar administration include, but are not limited to, bronchoalveolar lavage (BAL) according to methods well known to those skilled in the art, using as a lavage fluid a physiologically acceptable composition in which GM-CSF been dissolved or indeed by any other effective form of intrabronchial administration including the use of inhaled powders containing GM-CSF in dry form, with or without excipients, or the direct application of GM-CSF, in solution or suspension or powder form during bronchoscopy. Methods for intratracheal administration include, but are not limited to, blind tracheal washing with a similar solution of dissolved GM-CSF or a GM-CSF suspension, or the inhalation of nebulized fluid droplets containing dissolved GM-CSF or a GM-CSF suspension obtained by use of any nebulizing apparatus adequate for this purpose.

In another embodiment, intratracheal, intrabronchial or intraalveolar administration does not include inhalation of the product but the instillation or application of a solution of GM-CSF or a powder or a gel containing GM-CSF into the trachea or lower airways.

Other methods of administration may include using the following devices:

1. Pressurized nebulizers using compressed air/oxygen mixture
2. Ultrasonic nebulizers
3. Electronic micropump nebulizers (e.g. Aeroneb Professional Nebulizer)
4. Metered dose inhaler (MDI)
5. Dry powder inhaler systems (DPI), The aerosol may be delivered by via a) facemasks or b) via endotracheal tubes in intubated patients during mechanical ventilation (device 1, 2 and 3). The devices 4 and 5 can also be used by the patient without assistance provided that the patient is able to self-activate the aerosol device.

In certain embodiments, a composition comprising GM-CSF is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of GM-CSF in view of its structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the GM-CSF may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a GM-CSF may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of the GM-CSF concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The GM-CSF may be encapsulated in a microemulsion by any method generally known in the art.

In yet another embodiment, a GM-CSF may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. METHODS

In another aspect, the present invention provides a method of treating a subject having or suspected of having pulmonary dysfunction resulting from impaired alveolar macrophage development by administering to the subject an effective amount of granulocyte-macrophage colony stimulating factor (GM-CSF) via pulmonary airway administration. In another aspect, the present disclosure provides protection against respiratory tract infections (e.g., decreased susceptibility to infection) in a subject having or suspected of having impaired alveolar macrophage development by administering to the subject an effective amount of granulocyte-macrophage colony stimulating factor (GM-CSF) via pulmonary airway administration. In another aspect, the disclosure provides a method of preventing chronic lung disease, or broncho pulmonary dysplasia in a subject suspected having or suspected of having pulmonary dysfunction resulting from impaired alveolar macrophage development comprising administering to the subject an effective amount of granulocyte-macrophage colony stimulating factor (GM-CSF) via pulmonary airway administration. In another aspect the present disclosure provides a method of improving lung surfactant homeostasis in a subject suspected having or suspected of having pulmonary dysfunction resulting from impaired alveolar macrophage development comprising administering to the subject an effective amount of granulocyte-macrophage colony stimulating factor (GM-CSF) via pulmonary airway administration. In still another aspect, the present disclosure provides a method of increasing alveolar macrophage or alveolar macrophage precursor numbers in a subject having or suspected of having pulmonary dysfunction resulting from impaired alveolar macrophage development comprising administering to the subject an effective amount of granulocyte-macrophage colony stimulating factor (GM-CSF) via pulmonary airway administration. Suitable compositions comprising GM-CSF for use in the present methods are disclosed in Section I, above.

A "subject" includes, but is not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In embodiments where the animal is a mouse, the mouse may be a C57BL/6 mouse, a Balb/c mouse, a 129sv, or any other laboratory strain. In an exemplary embodiment, the subject is a C57BL/6J mouse. In a preferred embodiment, the subject is human.

In some embodiments, the subject is a neonatal subject. In some embodiments, the neonatal subject is preterm. As used herein, the term "preterm" generally describes human gestation resulting in birth prior to 37 weeks. Accordingly, "preterm" covers births occurring less than 35 weeks or less than or equal to 32 weeks of gestation. As described herein, preterm subjects have disrupted AM development relative to subjects born full term. For example, the number of AMs and AM precursors is reduced in preterm subjects relative to full term subjects. As used herein, the term "neonate" can refer to an infant less than thirty days old (e.g., less than one day old). In some embodiments, the subject is a preterm neonate. In a cohort of live-born infants who died in the early neonatal period, AMs were present in 33 of 46 (72%) infants who died before 48 hours of age but were apparent in the lungs of 50 of 54 (93%) infants who survived longer than 48 hours (E. Alenghat et al., Pediatrics 74,221-223 (1984)). The emergence of AMs in the lungs of neonates correlated with time since birth, consistent with the murine model in which AM precursors differentiate to mature AM shortly after birth. Accordingly, in some embodiments, a subject according to the disclosure is a subject having or suspected of having impaired AM development. In one aspect, a subject with impaired AM development is a preterm subject. In some embodiments, a subject with impaired AM development has reduced number of AMs and/or AM precursors relative to a reference value.

A reference value may represent a number of AMs and/or AM precursors of a control subject or represent number of AMs and/or AM precursors of a control population. In some examples, a number of AMs and/or AM precursors of a control subject or a control population may be determined by the same method as used for determining the number of AMs and/or AM precursors of the candidate subject. In some instances, the control subject or control population may refer to a healthy subject or healthy subject population of the same species (e.g., a human subject or human subject population having no disease). Alternatively, the control subject or control population may be an impaired AM development patient population who is responsive to GM-CSF disclosed herein. In other instances, the control subject or control population may be a septic arthritis, transient synovitis or osteomyelitis patient or septic arthritis, transient synovitis or osteomyelitis patient population who is non-responsive to the therapeutic agent.

By comparing the number of AMs and/or AM precursors of a candidate subject as disclosed herein and a reference value as also described herein, the subject can be identified as responsive or likely to be responsive or as not responsive or not likely to be responsive to treatment based on the assessing.

For example, when the reference value represents a number of AMs and/or AM precursors of subjects who are responsive to a therapy, derivation from such a reference value would indicate non-responsiveness to the therapy. Alternatively, when the reference value represents similar numbers of AMs and/or AM precursors of patients who are non-responsive to a therapy, derivation from such a reference value would indicate responsiveness to the therapy. In some instances, derivation means that the number of AMs and/or AM precursors (e.g., represented by a score) of a candidate subject is elevated or reduced as relative to a reference value, for example, by at least 5%, 10%, 20%, 30%, 40%, 50%, 60%, 70%, 80%, 90%, 100%, 150%, 200%, 300%, 400%, 500% or more above or below the reference value.

It is to be understood that the methods provided herein do not require that a reference value be measured every time a candidate subject is tested. Rather, in some embodiments, it is contemplated that the reference value can be obtained and recorded and that any test level can be compared to such a reference level. The reference level may be a single-cutoff value or a range of values.

By comparing the number of AMs and/or AM precursors of a candidate subject as disclosed herein and a reference value as also described herein, the subject can be identified as having or at risk for impaired AM development.

For example, when the reference value represents a similar number of AMs and/or AM precursors of healthy controls, derivation from such a reference value would indicate disease occurrence of risk for the disease. Alternatively, when the reference value represents the same gene signature of patients in inactive disease state, derivation from such a reference value would indicate active disease.

In some embodiments, the present disclosure provides a method of decreasing susceptibility to a respiratory tract infection in a subject with pulmonary dysfunction. In one aspect, the pulmonary dysfunction is a result of impaired AM development. In one aspect the subject has increased protection from a respiratory tract infection relative to a subject with pulmonary dysfunction and has not been treated with GM-CSF.

Infections may for example be an infection by bacteria, fungi, viruses, parasites. For example infection by parasites such as *plasmodium falciparum*. For example infection by one or more bacteria selected from the group consisting of *Achromobacter xylosoxidans, Acinetobacter calcoaceticus*, preferably *A. anitratus, A. haemolyticus, A. alcaligenes*, and *A. Iwoffii, Actinomyces israelii, Aeromonas hydrophilia, Alcaligenes* species, preferably *A. faecalis, A. odorans* and *A. denitrificans, Arizona hinshawii, Bacillus anthracis, Bacillus cereus, Bacteroides fragilis, Bacteroides melaminogenicus, Bordetella pertussis, Borrelia burgdorferi, Borrelia recurrentis, Brucella* species, preferably *B. abortus, B. suis, B. melitensis* and *B. canis, Calymmatobacterium granulomatis, Campylobacter fetus* ssp. *intestinalis, Campylobacter fetus* ssp. *jejuni, Chlamydia* species, preferably *C. psittaci* and *C. trachomatis, Chromobacterium violaceum, Citrobacter* species, preferably *C. freundii* and *C. diversus, Clostridium botulinum, Clostridium perfringens, Clostridium difficile, Clostridium tetani, Corynebacterium diphtheriae, Corynebacterium*, preferably *C. ulcerans, C. haemolyticum* and *C. pseudotuberculosis, Coxiella bumetii, Edwardsiella tarda, Eikenella corrodens, Enterobacter*, preferably *E. cloacae, E. aerogenes, E. hafniae* (also named *Hafnia alvei*) and *E. agglomerans, Erysipelothrix rhusiopathiae, Escherichia coli, Flavobacterium meningosepticum, Francisella tularensis, Fusobacterium nucleatum, Gardnerella vaginalis, Haemophilus ducreyi, Haemophilus influenzae, Helicobacter* species, *Klebsiella* species, preferably *K. pneumoniae, K. ozaenae* og *K. rhinoscleromatis, Legionella* species, *Leptospira interrogans, Listeria monocytogenes, Moraxella* species, preferably *M. lacunata* and *M. osloensis, Mycobacterioum bovis, Mycobacterium leprae, Mycobacterium tuberculosis, Mycoplasma* species, preferably *M. pneumoniae, Neisseria gonorrhoeae, Neisseria meningitidis, Nocardia* species, preferably *N. asteroides* and *N. brasiliensis, Pasterurella haemolytica, Pasteurella multocida, Peptococcus magnus, Plesiomonas shigelloides, Pneumococci, Proteus* species, preferably *P. mirabilis, P. vulgaris, P. rettgeri* and *P. morganii* (also named *Providencia rettgeri* and *Morganella morganii* respectively), *Providencia* species, preferably *P. alcalifaciens, P. stuartii* and *P. rettgeri* (also named *Proteus rettgeri*), *Pseudomonas aeruginosa, Pseudomonas mallei, Pseudomonas pseudomallei, Rickettsia, Rochalimaia henselae, Salmonella* species, preferably *S. enteridis, S. typhi* and *S. derby*, and most preferably *Salmonella* species of the type *Salmonella* DT104, *Serratia* species, preferably *S. marcescens, Shigella dysenteriae, S. flexneri, S. boydii* and *S. sonnei, Spirillum minor, Staphylococcus aureus, Staphylococcus epidermidis, Staphylococcus saprophyticus, Streptobacillus moniliformis, Streptococcus*, preferably *S. faecalis, S. faecium* and *S. durans, Streptococcus agalactiae, Streptococcus pneumoniae, Streptococcus pyogenes, Treponema carateum, Treponema pallidum, Treponema pertenue*, preferably *T. pallidum, Ureaplasma urealyticum, Vibrio cholerae, Vibrio parahaemolyticus, Yersinia enterocolitica*, and *Yersinia pestis*.

Infections also comprise protozoan infections such as, but not limited to, Trichomonas infections, such as *Pentatrichomonas* infections. For example *T. buccalis, T. tenax, T. foetus, T. galli'nae, T. gallina'rum, T. ho'minis, T. intestinalis, T. te'nax, T. vaginalis*.

In other embodiments of the invention GM-CSF may be used for the treatment of any condition caused by fungal infections including, but not limited to: Aspergillosis, Blastomycosis, Candidiasis, Coccidioidomycosis, Cryptococcosis, Histoplasmosis, Paracoccidiomycosis, Sporotrichosis, Zygomycosis, *pneumocystis carinii*. The composition may also be used to treat fungal infections in conditions such as Chromoblastomycosis, Mycotic keratitis, Endogenous oculomycosis, Extension oculomycosis, Lobomycosis, Mycetoma, Nail, Hair, and Skin diseases (for example Onychomycosis (Tinea unguium), Piedra, Pityriasis versicolor, Tinea barbae, Tinea capitis, Tinea corporis, Tinea cruris, Tinea favosa, Tinea nigra, Tinea pedis), Otomycosis, Phaeohyphomycosis, Rhinosporidiosis.

In another aspect the present disclosure provides a method of improving lung surfactant homeostasis in a subject. In some embodiments, the subject is suspected having or suspected of having pulmonary dysfunction. In one aspect the pulmonary dysfunction results from impaired alveolar macrophage development. In general, the method comprises administering to the subject an effective amount of granulocyte-macrophage colony stimulating factor (GM-CSF) via pulmonary airway administration. Lung surfactant homeostasis can be assayed by determining the levels of surfactant protein-A (SP-A) and/or surfactant protein-D (SP-D). In some embodiments, SP-D is reduced in a subjected treated with a composition as disclosed herein. In one aspect, SP-D is reduced relative to the subject prior to treatment. In another aspect, SP-D is reduced relative to a subject having impaired AM development and/or lung surfactant homeostatis.

In another aspect, the disclosure provides a method of preventing chronic lung disease, or broncho pulmonary dysplasia in a subject suspected having or suspected of having pulmonary dysfunction resulting from impaired alveolar macrophage development comprising administering to the subject an effective amount of granulocyte-macrophage colony stimulating factor (GM-CSF) via pulmonary airway administration. Chronic lung disease includes, but is not limited to, asthma, chronic obstructive pulmonary disease (COPD), pulmonary fibrosis, and pneumonitis. Bronchopulmonary dysplasia (BPD), is a serious lung condition that affects newborns. BPD mostly affects premature newborns who need oxygen therapy, which is oxygen given through nasal prongs, a mask, or a breathing tube.

Most newborns who develop BPD are born more than 10 weeks before their due dates, weigh less than 2 pounds at birth, and have breathing problems. Infections that occur before or shortly after birth also can contribute to BPD. Most babies who develop BPD are born with respiratory distress syndrome (RDS). RDS is a breathing disorder that mostly affects premature newborns. If premature newborns still require oxygen therapy by the time they reach 36 weeks gestation, they are diagnosed with BPD. Some newborns may need long-term oxygen or breathing support from nasal continuous positive airway pressure (NCPAP) machines, ventilators, and medicines like bronchodilators. They may continue to have breathing problems throughout childhood and even into adulthood. To confirm a diagnosis of BPD, tests, such as: Chest X-rays, blood tests, and/or echocardiography can be performed.

In general, it is contemplated that compositions of the invention may be administered to a subject at birth or shortly thereafter. For example, shortly after birth may include but is not limited to, within about 1 minute, within about 2 minutes, within about 3 minutes, within about 4 minutes, within about 5 minutes, within about 10 minutes, within about 15 minutes, within about 20 minutes, within about 25 minutes, within about 30 minutes, within about 35 minutes, within about 40 minutes, within about 45 minutes, within about 50 minutes, within about 55 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, within about 1 day, within about 2 days, within about 3 days, within about 4 days, within about 5 days, within about 6 days, within about 7 days after birth.

Compositions may be administered to a subject once, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 or more times, and/or they may be administered about every hour, about every 2 hours, about every 3 hours, about every 4 hours, about every 5 hours, about every 6 hours, about every 7 hours, about every 8 hours, about every 9 hours, about every 10 hours, about every 11 hours, about every 12 hours, about every 13 hours, about every 14 hours, about every 15 hours, about every 16 hours, about every 17 hours, about every 18 hours, about every 19 hours, about every 20 hours, about every 21 hours, about every 22 hours, about every 23 hours, about every 24 hours, or about every day, about every 2 days, about every 3 days, about every 4 days, about every 5 days, about every 6 days, about every 7 days, or about every week, about every 2 weeks, about every 3 weeks, about every 4 weeks, about every 5 weeks, or about every month, about every 2 months, about every 3 months, 4 months, 5 months, 6 months, 7 months, 8 months, 9 months, about every 10 months, about every 11 months, about every 12 months, or any range or combination derivable therein.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introution to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds.(1985»; Transcription and Translation (B. D. Hames & S.J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Inhaled GM-CSF in Neonatal Mice Provides Durable Protection Against Bacterial Pneumonia Pneumonia poses profound health threats to preterm infants. Alveolar macrophages (AMs) eliminate inhaled pathogens while maintaining surfactant homeostasis. As AM development only occurs perinatally, therapies that accelerate AM maturation in preterms may improve outcomes. Therapeutic rescue of AM development was tested in mice lacking the actin-bundling protein L-plastin (LPL), which exhibit impaired AM development and increased susceptibility to pneumococcal lung infection. Airway administration of recombinant granulocyte-macrophage colony-stimulating factor (GM-CSF) to $LPL^{-/-}$ neonates augmented AM production. Airway administration distinguishes the delivery route from prior human infant trials. Adult $LPL^{-/-}$ animals that received neonatal GM-CSF were protected from experimental pneumococcal challenge. No detrimental effects on surfactant metabolism or alveolarization were observed. Airway recombinant GM-CSF administration thus shows therapeutic promise to accelerate neonatal pulmonary immunity, protecting against bacterial pneumonia.

Methods

Study Design

The primary objective of this study was to test the protective effect of administering rGM-CSF to neonatal $LPL^{-/-}$ pups (in the temporal window of AM development) during subsequent bacterial lung infection. This objective was defined before initiation of the experiments and data analysis. The experimental design was a controlled laboratory experiment using genetically modified mice. Pups within each litter of mice were randomly assigned to receive intranasal rGM-CSF or PBS (control). In one set of experiments, pups within litters were randomized to receive subcutaneous rGM-CSF or PBS (control).

Figure 5:
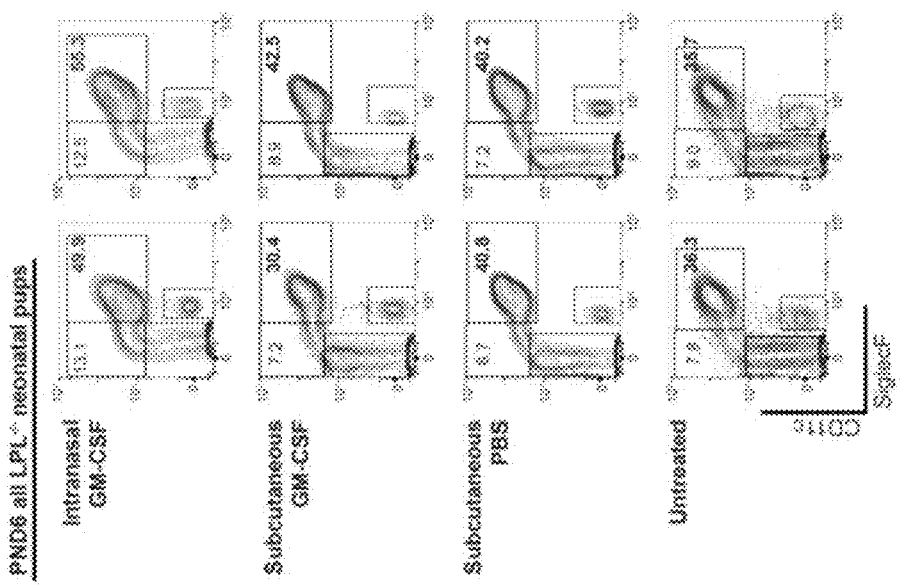
FIG. 5 shows no increase in mature AMs following the subcutaneous administration of rGM-CSF (20 ng) to $LPL^{-/-}$ neonatal pups on DOB, PND1, and PND2. Flow cytometry of whole lung homogenates from $LPL^{-/-}$ neonatal mice treated as indicated and sacrificed on PND6. Gated on $CD45^+$, $F4/80^+/CD11b^+$ cells as shown in FIG. 1.

Mice $LPL^{-/-}$ mice fully back-crossed to the C57BL/6 background have been described (E. M. Todd et al., Blood 128, 2785-2796 (2016); L. E. Deady et al., Infect. Immun. 82, 1982-1993 (2014)). WT and $LPL^{-/-}$ mice were bred and cohoused in the same specific pathogen-free barrier animal facility. Human rGM-CSF (20 ng in 6 µl of PBS per inoculation) was administered intranasally to pups in all experiments except for the data presented in FIG. 5. In FIG. 5, some neonatal pups received 20 ng of rGM-CSF in 10 µl of PBS via subcutaneous injection. Litters of WT and $LPL^{-/-}$ pups were divided such that approximately half received PBS and half received rGM-CSF and such that littermate controls were used to discern the effects of rGM-CSF. Mice matched for sex and age were used in all experiments, which were conducted in accordance with a protocol approved by the Institutional Animal Care and Use Committee at Washington University School of Medicine (WUSM).

Cell Isolation and Media

BAL was performed as described (L. E. Deady et al., Infect. Immun. 82, 1982-1993 (2014)), and cells were quantified by flow cytometry (E. M. Todd et al., Blood 128, 2785-2796 (2016)). Lungs were homogenized using collagenase D (2.5 mg/ml) in Hanks' balanced salt solution and 3% fetal calf serum (E. M. Todd et al., Blood 128, 2785-2796 (2016)).

Flow Cytometry

Commercial antibodies to the indicated murine antigens were used: CD11c-phycoerythrin (PE)/Cy7, CD11c-allophycocyanin (APC) (N418), CD11c-APCCy7 (N418), CD64-PE (X54-5/7.1), F4/80-PerCP/Cy5.5, F4/80-APC (BM8), I-Ak-PE (10-3.6), Ly-6C-PacBlue (HK1.4), Ly-6C-BV510 (HK1.4), CD45-PacBlue (30-F11), CD45-BV785 (30-F11), and Ly-6G-PacBlue (1A8) (all from BioLegend San Diego, Calif.); CD11b-fluorescein isothiocyanate (M1/70), CD11b-PeCy7 (M1/70), and CD11c-PE (N418) (all from eBioscience, San Diego, Calif.); CD45-BV510 (104), SiglecF-PE, SiglecF-Alexa Fluor 647, SiglecF-APC700, and (E50-2440) Ly6G-BUV395 (1A8) (all from BD Biosciences, San Jose, Calif.); and MerTK-PE/Cy7 (DS5MMER) (from Invitrogen, Carlsbad, Calif.). BrdU labeling was performed using the BrdU-APC labeling Kit (BD Biosciences) according to the manufacturer's protocol. Cells were acquired either on the BD Biosciences LSRFortessa or with a BD FACScan flow cytometer with DxP multicolor upgrades by Cytek Development Inc. (Woodland Park, N.J.) and then analyzed using FlowJo software (FlowJo LLC, Ashland, Oreg.). Samples were preincubated with Fc-block [Hybridoma 2.4 G2, American Type Culture Collection (ATCC)].

Infection

*Streptococcus pneumoniae* [ATCC 6303, serotype 3; $5 \times 10^4$ CFU per animal in 20 µl of Dulbecco's PBS) was instilled intratracheally as before (E. M. Todd et al., Blood 128, 2785-2796 (2016); L. E. Deady et al., Infect. Immun. 82, 1982-1993 (2014)). Blood was obtained for quantitative culture 24 hours after inoculation. Mice were monitored at least twice daily using a "humane end points" scoring system that included daily weight and temperature monitoring and observation of animals' grooming, activity, behavior, and respirations. Animals that lost >20% of starting weight or that scored >5 on the clinical observation score were euthanized. Tissues were harvested for either flow cytometry or for histology. Histological specimens were preserved in formalin (10%) and then embedded in paraffin. Sections were prepared and stained with hematoxylin and eosin by the Division of Comparative Medicine core facility at WUSM. Histological sections were reviewed by an independent veterinary pathologist.

Surfactant Protein Analysis

Concentrations of SP-A (Biotang Inc.) and SP-D (R&D Systems) in whole-lung homogenates were determined by enzyme-linked immunosorbent assay according to the manufacturer's protocol.

Statistics

Nonparametric tests were used to compare non-Gaussian data. All quantitative data are fully displayed in graphs, as they are represented either with box and whisker plots (line shows the median value, box shows 25th to 75th percentiles, and whiskers show minimum and maximum values) or with symbols indicating each value. Comparisons of two groups were made with the Mann-Whitney U test, and comparisons of multiple groups used the Kruskal-Wallis test. Survival curves were compared using the log-rank Mantel-Cox test. A P value of <0.05 was considered statistically significant.

As these studies were performed to generate preliminary data and demonstrate feasibility, power calculations could not be performed in advance; the number of experiments to be performed was determined on the basis of the number of experiments required in prior reports to demonstrate differences between groups of animals (E. M. Todd et al., Blood 128, 2785-2796 (2016); L. E. Deady et al., Infect. Immun. 82, 1982-1993 (2014)). End points of all experiments were determined in advance of performing the experiment. All results of all experiments that were technically interpretable were included. No outliers from any experiment were excluded. The number of animals and replicates for each experiment is provided in the figure or legend.

Results (i) Neonatal Administration of rGM-CSF Enhances AM Population in $LPL^{-/-}$ mice.

It was previously shown that $LPL^{-/-}$ mice exhibit defective AM development due to the impaired migration of pre-AM precursors into the alveolar space (E. M. Todd et al., Blood 128, 2785-2796 (2016)). Impaired migration results in reduced numbers of mature AMs and subsequent susceptibility to pneumococcal lung infection. Notably, AM precursors in $LPL^{-/-}$ mice retain responsiveness to the required growth factor GM-CSF (E. M. Todd et al., Blood 128, 2785-2796 (2016)). The present study was undertook to determine whether perinatal AM development could be augmented by the exogenous intranasal administration of GM-CSF and provide durable protection against pneumococcal lung infection.

Figure 1B:
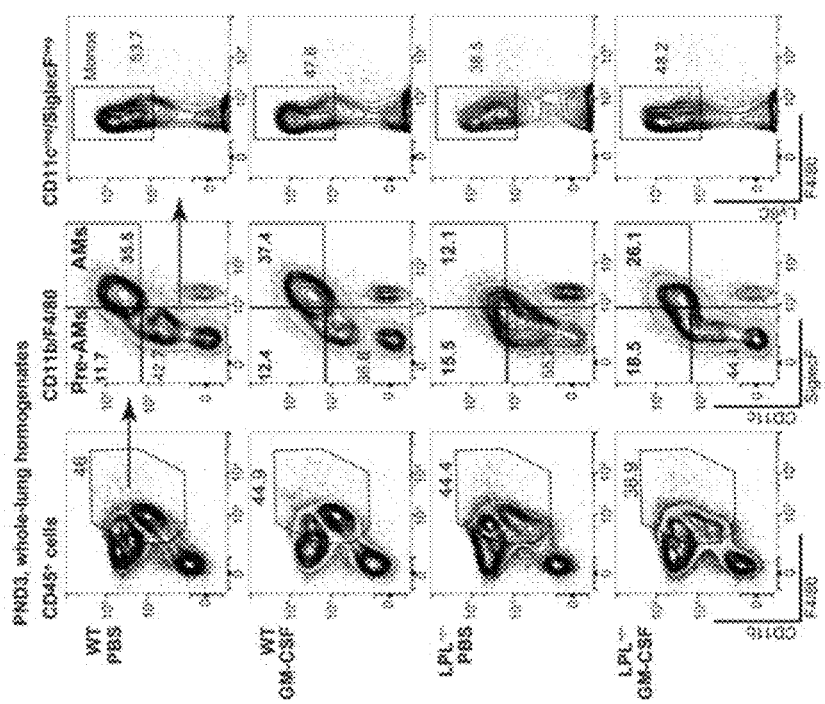
Figure 1C:
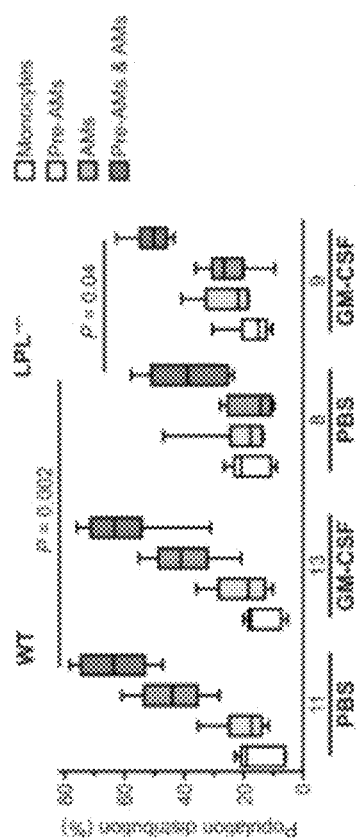

To test whether the airway administration of GM-CSF would augment AM maturation during the normal physiological window of development, recombinant GM-CSF (rGM-CSF) was intranasally administered to wild-type (WT) and $LPL^{-/-}$ mouse pups or phosphate-buffered saline (PBS) to control mice on the day of birth (DOB), PND1, and PND2 (FIG. 1A). Mice were euthanized on PND3, and populations of fetal monocytes, pre-AMs, and AMs in whole-lung homogenates were determined by flow cytometry (FIG. 1B) (M. Guilliams et al., J. Exp. Med. 210, 1977-1992 (2013)). As previously observed (E. M. Todd et al., Blood 128, 2785-2796 (2016)), untreated $LPL^{-/-}$ pups showed no deficiencies in fetal monocyte or pre-AM populations compared to WT pups but did exhibit a reduced percentage of mature AMs. The administration of rGM-CSF to $LPL^{-/-}$ pups increased the proportion of CD11c+ maturing cells (combined pre-AMs and AMs; FIG. 1C), while these proportions were unchanged by rGM-CSF administration to WT pups. Administering the same amount of rGM-CSF (20 ng) to $LPL^{-/-}$ pups via subcutaneous injection (systemic administration) on DOB, PND1, and PND2 did not enhance AM maturation, as assessed on PND6 (FIG. 5).

Figure 1D:
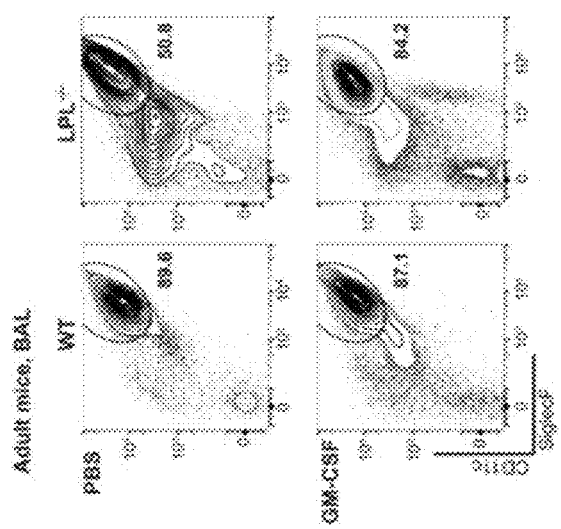
Figure 1E:
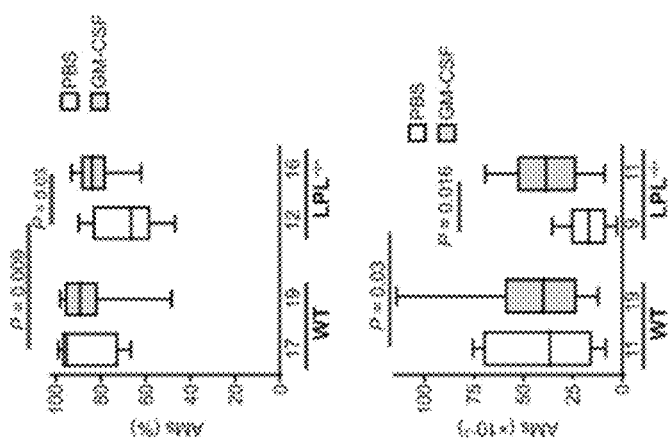

To determine whether neonatal rGM-CSF administration elicited durable change in AM numbers, the percentage and numbers of AMs recovered from adult (defined as week old) animals that had received intranasally either PBS or rGM-CSF as neonatal pups was analyzed. As previously observed (E. M. Todd et al., Blood 128, 2785-2796 (2016)), untreated adult $LPL^{-/-}$ mice exhibited reduced AMs compared with WT mice (FIG. 1D and FIG. 1E). However, $LPL^{-/-}$ mice that had received rGM-CSF as pups harbored significantly higher numbers of AMs in bronchoalveolar lavage (BAL) fluid (FIG. 1E), while similarly treated WT mice demonstrated no alteration in AMs. Thus, exogenous rGM-CSF enhanced AM production under conditions where maturation was impaired but did not alter normal AM development.

Figure 6A:
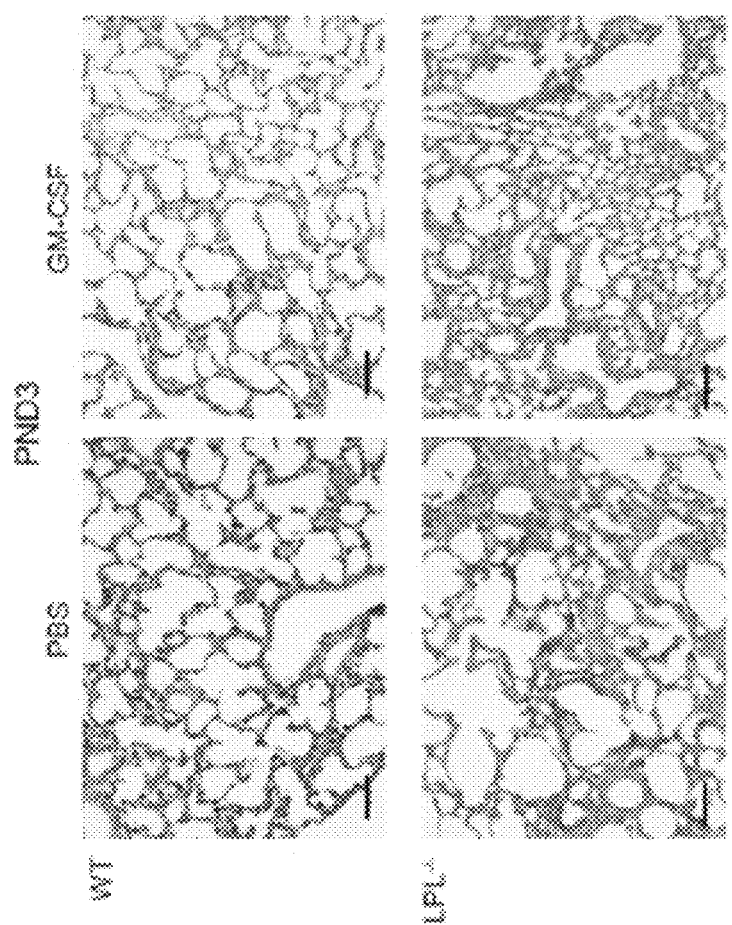
FIG. 6A and FIG. 6B shows no disruption of alveolarization observed after intranasal neonatal rGM-CSF therapy.
Figure 6B:
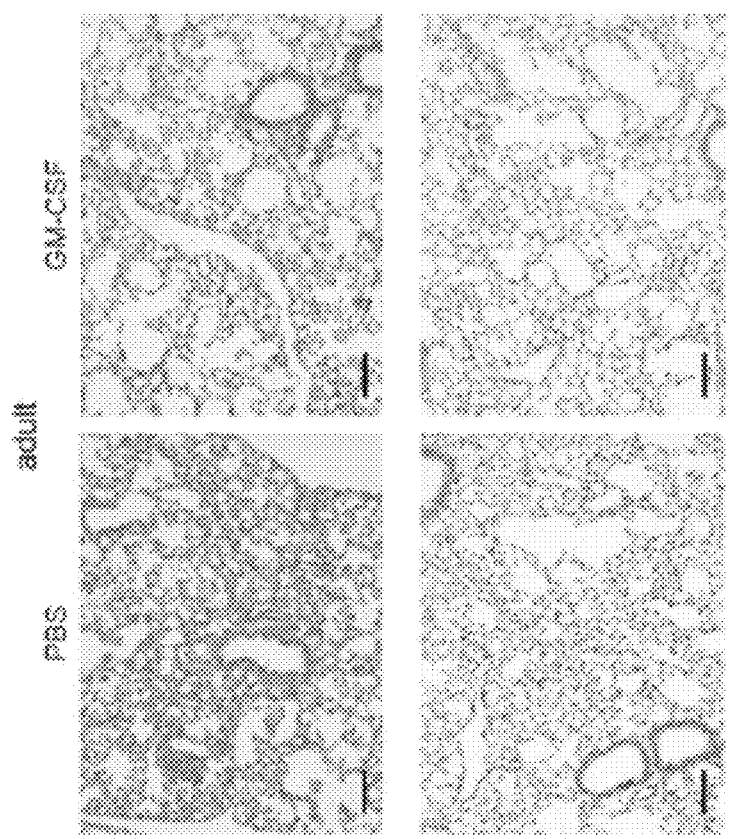

GM-CSF has been considered pro-inflammatory in the lung (R. Puljic et al., Eur. J. Pharmacol. 557, 230-235 (2007)), and excess inflammation has been associated with the disruption of alveolarization in neonatal mice (T. S. Blackwell et al., J. Immunol. 187, 2740-2747 (2011)). To test whether the exogenous administration of rGM-CSF to neonatal pups interfered with alveolarization in the developing lungs, histological sections of WT and $LPL^{-/-}$ pups (PND3) and adults that received either PBS or rGM-CSF were examined by a veterinary pathologist. No disruption of alveolarization was observed (FIG. 6A and FIG. 6B).

Neonatal rGM-CSF Administration Protected Adult $LPL^{-/-}$ Mice from Infection.

Figure 2A:
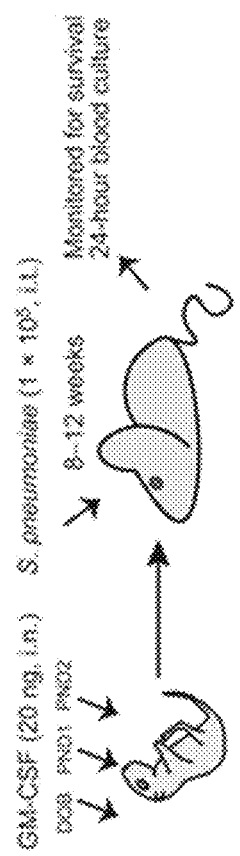
FIG. 2A, FIG. 2B, FIG. 2C, FIG. 2D, FIG. 2E, and FIG. 2F show adult $LPL^{-/-}$ mice that received neonatal rGM-CSF therapy are protected from pneumococcal infection.
Figure 2B:
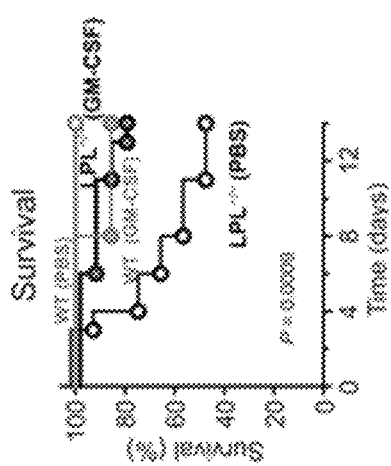
Figure 2C:
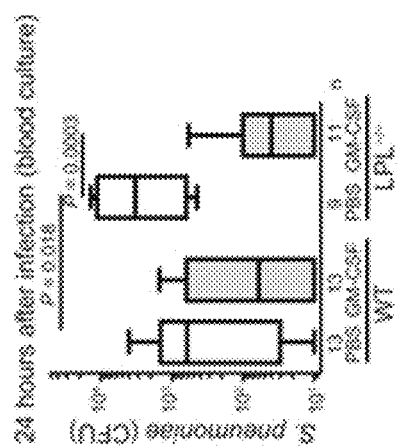
Figure 2D:
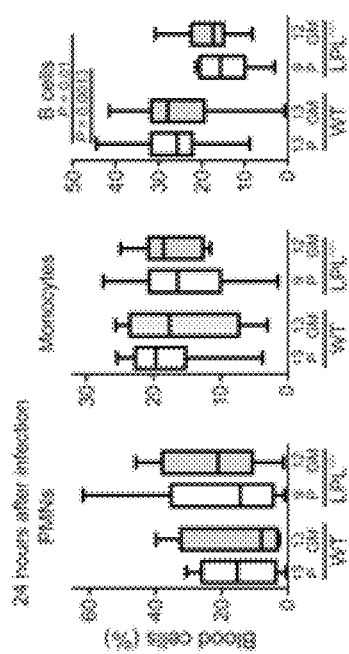

To determine whether enhanced neonatal AM development protected mice from subsequent infection, adult $LPL^{-/-}$ mice that received neonatal rGM-CSF were challenged intratracheally with pneumococcus (FIG. 2A). The same inoculum used in prior studies was selected, in which about 10 to 20% of WT animals would be expected to succumb, while up to 70 to 80% of $LPL^{-/-}$ mice might succumb. This sizable differential in susceptibility provides the optimal conditions for observing an effect of neonatal rGM-CSF therapy (E. M. Todd et al., Blood 128,2785-2796 (2016); L. E. Deady et al., Infect. Immun. 82,1982-1993 (2014)). As anticipated, untreated $LPL^{-/-}$ mice were more susceptible to pneumococcal pneumonia than were WT mice (FIG. 2B). However, adult $LPL^{-/-}$ mice that had received neonatal rGM-CSF therapy were significantly protected from mortality, while the already low mortality in infected WT mice was unaltered by neonatal rGM-CSF therapy (FIG. 2B). Quantitative blood cultures obtained 24 hours after pneumococcal inoculation revealed that untreated $LPL^{-/-}$ mice suffered from augmented dissemination (FIG. 2C), as reported previously (L. E. Deady et al., Infect. Immun. 82,1982-1993 (2014)) and aligned with their increased mortality. The neonatal rGM-CSF treatment of $LPL^{-/-}$ mice reduced pneumococcal bloodstream dissemination in infected adults to match that in WT animals, showing that the neonatal administration of inhaled rGM-CSF provided sustained rescue of pulmonary host defense. An analysis of peripheral blood 24 hours after infection revealed no significant difference in the percentages of circulating neutrophils or monocytes in infected WT or $LPL^{-/-}$ mice treated with neonatal PBS or rGM-CSF. $LPL^{-/-}$ mice exhibit reduced B cell maturation (E. M. Todd et al. J. Immunol. 187,3015-3025 (2011)), which was expectedly unchanged by neonatal rGM-CSF intranasal administration (FIG. 2D). Thus, no evidence that intranasal neonatal rGM-CSF treatment altered systemic host immune responses was detected (FIG. 2D) while protecting against pulmonary infection (FIG. 2B and FIG. 2C).

Figure 2E:
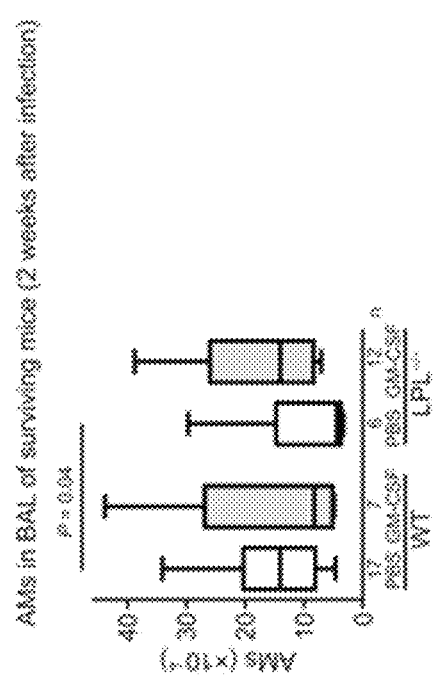
Figure 2F:
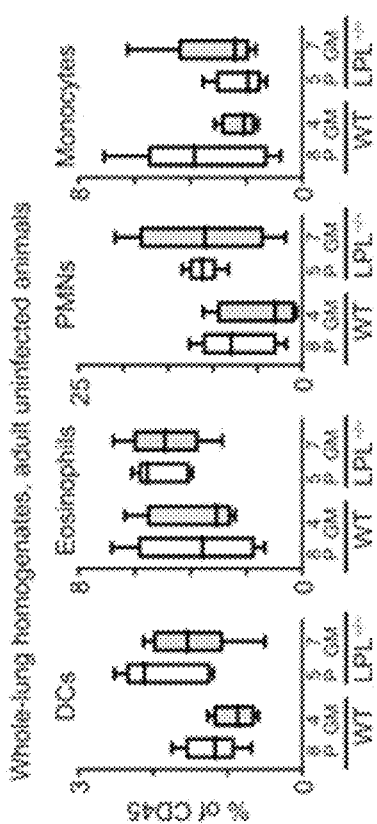

AMs in the BAL of adult animals that survived 2 weeks after intratracheal pneumococcal inoculation were also quantified. AM numbers in control and rGM-CSF-treated WT animals were equivalent. Untreated $LPL^{-/-}$ mice again exhibited reduced AM numbers compared to WT animals, while rGM-CSF-treated $LPL^{-/-}$ mice harbored AM numbers equivalent to those of WT animals (FIG. 2E). No changes in the proportions of other pulmonary innate immune cell types [dendritic cells (DCs), eosinophils, neutrophils, or monocytes] preceding infection were observed (FIG. 2F). Protection from pneumococcal infection thus correlated specifically with increased AM populations.

Neonatal rGM-CSF Administration Enhances AM and AM Precursor Proliferation

Figure 3A:
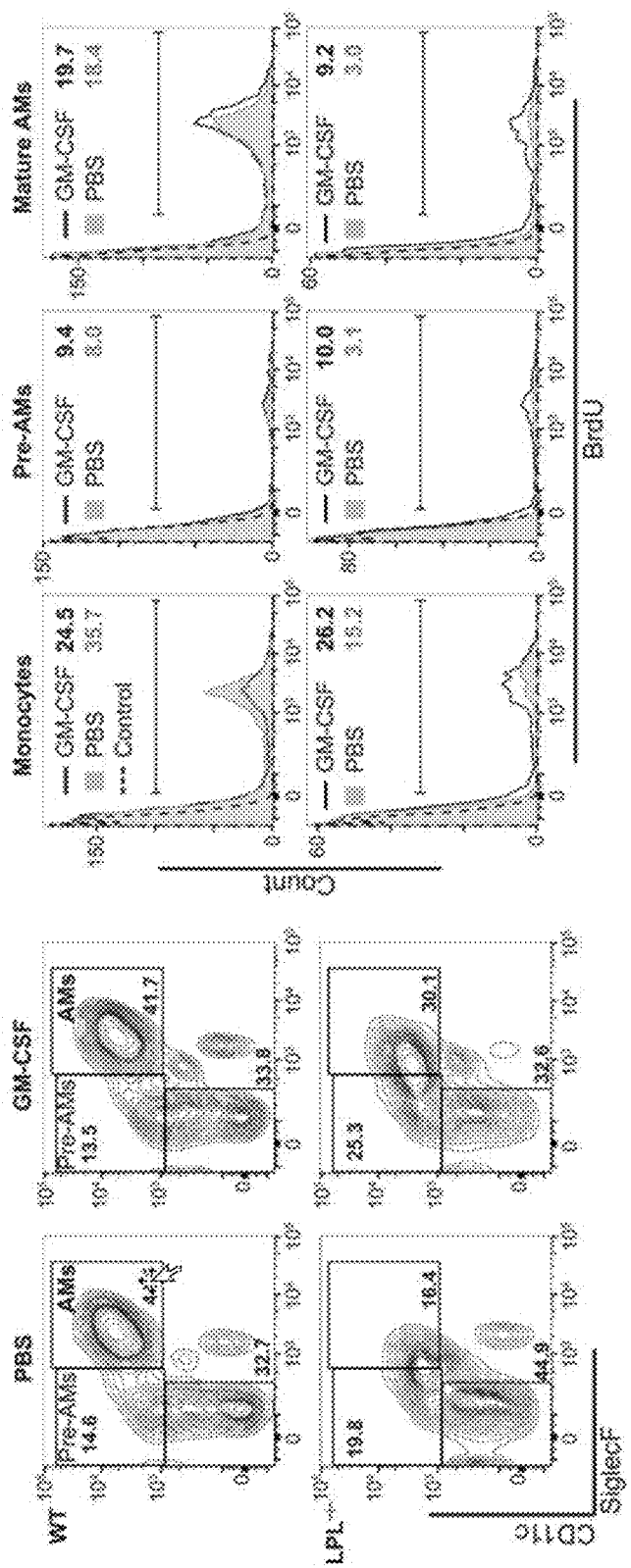
FIG. 3A, FIG. 3B, and FIG. 3C show rGM-CSF administration increased pre-AM proliferation in LPL–/– pups.
Figure 3B:
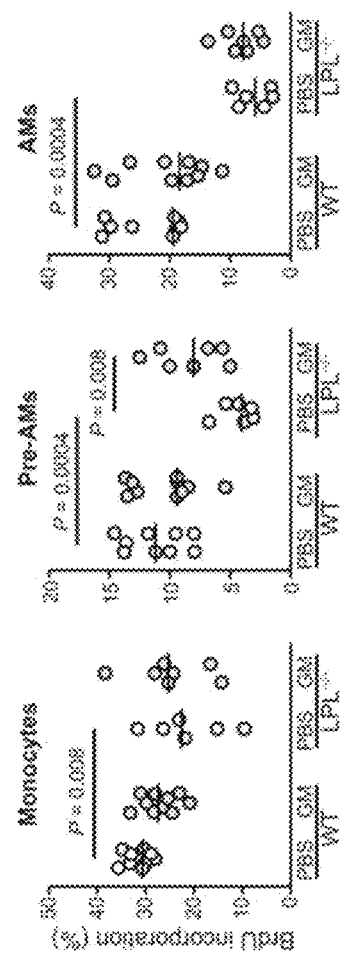

Next, it was sought to define a mechanism by which exogenous rGM-CSF therapy enhanced AM neonatal development. It had been previously shown that the migration of AM precursors into the alveoli is impaired in the absence of LPL. While it is not obvious how rGM-CSF could overcome this migration defect, it was hypothesized that exogenous rGM-CSF could increase the proliferation of precursor cells that do successfully reach the alveoli in $LPL^{-/-}$ pups—in other words, acting on cells "already there." Furthermore, the contribution of proliferation to the increase in lung-resident monocyte, pre-AM, and AM populations during neonatal development has not been previously assessed. Therefore, 5-bromo-2'-deoxyuridine (BrdU) incorporation into monocytes, pre-AMs, and AMs was quantified in PND3 pups treated intranasally with PBS or rGM-CSF (FIG. 3A). AMs and precursors were identified using surface expression of CD11b, F4/80, CD11c, SiglecF, and Ly6C as previously defined [(FIG. 3B and (M. Guilliams etal., J. Exp. Med. 210,1977-1992 (2013))]. In untreated WT pups, it was noted proliferation in all three subpopulations, with substantial BrdU incorporation into fetal monocytes and AMs; meanwhile, BrdU incorporation into all three cell types was diminished in LPL$^{-/-}$ pups (FIG. 3A and FIG. 3B). Notably, neonatal rGM-CSF treatment significantly increased pre-AM proliferation by threefold in LPL$^{-/-}$ pups (FIG. 3B); thus, one mechanism by which rGM-CSF restores mature AM numbers in LPL$^{-/-}$ mice is by enhancing the proliferation of precursors that do succeed in reaching the alveolar space. Intranasal rGM-CSF therapy had no effect on the proliferation of pre-AMs or AMs in WT mice, again indicating that rGM-CSF therapy exerts little, if any, effect on AM development that is proceeding normally (FIG. 3B).

Figure 3C:
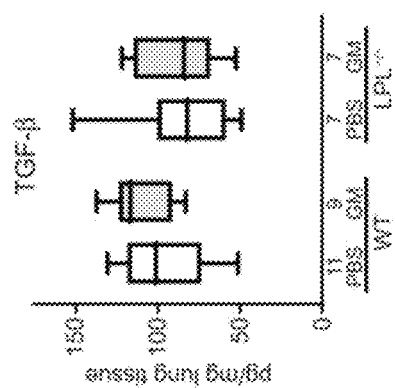

Recently, the autocrine production of transforming growth factor-β (TGF-β) has been shown to be essential for AM development and maintenance (X. Yu et al., Immunity 47,903-912.e4 (2017)). It had not previously been evaluated whether TGF-β production by AMs was altered by LPL deficiency. Furthermore, if TGF-β were dependent on LPL for generation, then a second mechanism of AM rescue by rGM-CSF could be by augmenting TGF-β production. Refuting this possibility, no difference in the whole-lung TGF-β concentration in PND3 WT or LPL$^{-/-}$ pups that had received PBS or rGM-CSF were found (FIG. 3C).

(iv) Neonatal rGM-CSF Improves Surfactant Homeostasis in LPL$^{-/-}$ Mice

Figure 4A:
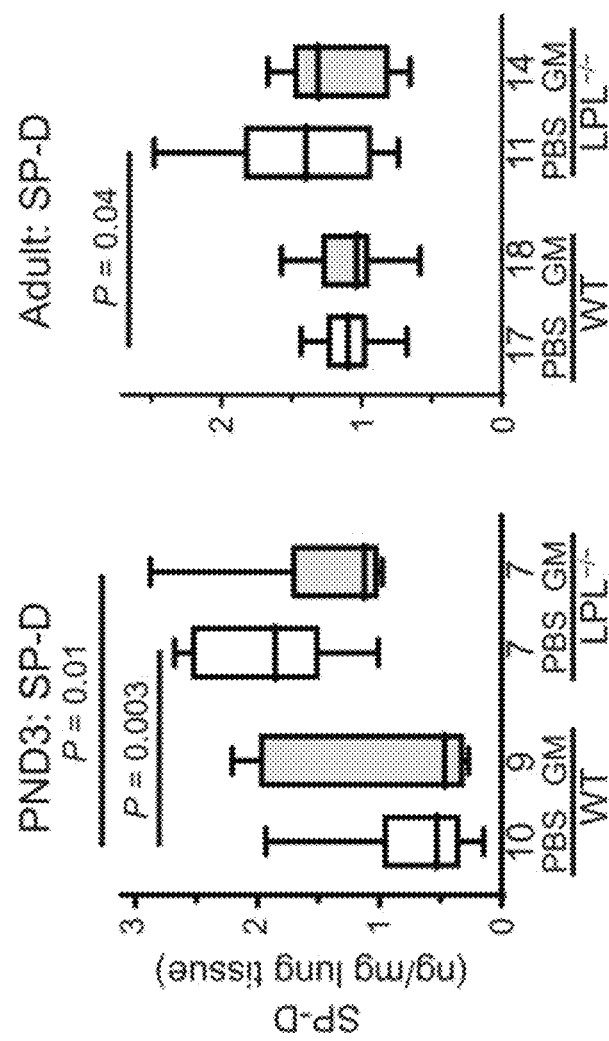
FIG. 4A and FIG. 4B show neonatal rGM-CSF corrects increased SP-D in $LPL^{-/-}$ mice.
Figure 4B:
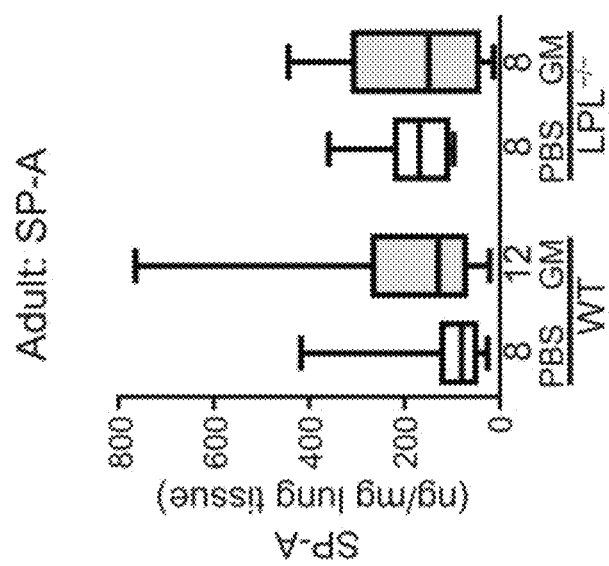
Figure 7A:
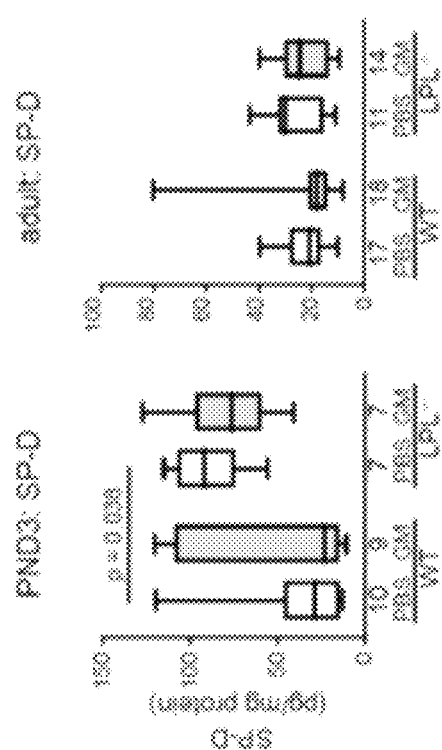
FIG. 7A and FIG. 7B show increased SP-D in $LPL^{-/-}$ PND3 neonatal pups.
Figure 7B:
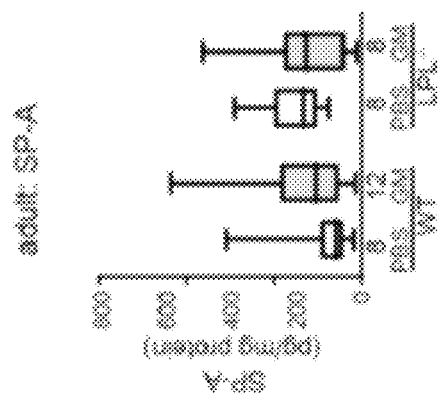

In addition to their critical role in host defense, AMs are essential to surfactant metabolism. Surfactant is produced by alveolar epithelial type II cells but taken up and catabolized in part by AMs, a process stimulated by GM-CSF. Animals deficient in GM-CSF or the GM-CSF receptor suffer from primary alveolar proteinosis, a progressive and ultimately fatal accumulation of surfactant protein in the alveoli (B. C. Trapnell et al., Annu. Rev. Physiol. 64,775-802 (2002); B. C. Trapnell et al., Curr. Opin. Immunol. 21,514-521 (2009); and T. Suzuki et al., Nature 514,450-454 (2014)). Although LPL$^{-/-}$ animals have not exhibited overt evidence of progressive lung disease (E. M. Todd et al., Blood 128,2785-2796 (2016); L. E. Deady et al., Infect. Immun. 82, 1982-1993 (2014)), surfactant proteins were not previously formally assessed in these mice. In addition, it was determined whether neonatal rGM-CSF treatment would alter surfactant catabolism in WT or LPL$^{-/-}$ mice. Surfactant protein D (SP-D) and SP-A were therefore quantified in WT and LPL$^{-/-}$ mice that had received intranasally either PBS or rGM-CSF as pups (FIG. 4). In PND3 and adult LPL$^{-/-}$ mice, the amount of SP-D per milligram of lung tissue was increased in LPL$^{-/-}$ whole-lung homogenates compared to untreated WT mice (FIG. 4A). Neonatal rGM-CSF therapy in LPL$^{-/-}$ mice partially ameliorated the increase in SP-D by PND3 and normalized SP-D concentrations by adulthood while not altering SP-D levels in WT mice (FIG. 4A). SP-A concentrations were not altered in the lungs of adult untreated LPL$^{-/-}$ mice and were not affected by neonatal rGM-CSF therapy (FIG. 4B). An analysis of SP-D and SP-A protein amounts compared to total lung protein revealed similar trends (FIG. 7). Therefore, neonatal rGM-CSF therapy did not alter surfactant metabolism in WT mice but ameliorated defects in LPL$^{-/-}$ mice associated with reduced AM production.

Discussion

Here, a preclinical model of impaired AM development was used to show that GM-CSF, a readily available, U.S. Food and Drug Administration-approved therapy, can be administered safely to the airways of newborn mice to accelerate AM maturation (FIG. 1) and protect otherwise susceptible animals from bacterial pneumonia (FIG. 2). One mechanism by which rGM-CSF rescues AM development in LPL$^{-/-}$ mice is by significantly increasing pre-AM proliferation (FIG. 3B) without affecting levels of TGF-β or disrupting alveolarization or normal surfactant homeostasis (FIG. 4 and FIG. 6). It is proposed that the translation of neonatal GM-CSF therapy to human infants could have a direct impact on improving outcomes of respiratory disease in preterm neonates, a benefit that would not have been apparent in prior studies that either subcutaneously or intravenously administered systemic GM-CSF (R. Carr et al., Lancet 373, 226-233 (2009); R. Carr et al., Cochrane Database Syst. Rev. 2003, CD003066 (2003).). Our work shows that the route and timing of GM-CSF administration—directly to the airways, in the first 24 hours of life, to mimic the physiological burst of GM-CSF production that naturally occurs (M. Guilliams et al., J. Exp. Med. 210, 1977-1992 (2013))—could exert effects very different from those previously observed when GM-CSF was administered systemically and, later, postnatally. In addition, the present studies expand on prior work revealing that LPL is an essential regulator of AM development (E. M. Todd et al., Blood 128, 2785-2796 (2016); L. E. Deady et al., Infect. Immun. 82, 1982-1993 (2014)); it is now showen that beyond supporting the migration and adhesion of AMs and AM precursors into the alveoli (E. M. Todd et al., Blood 128, 2785-2796 (2016)), LPL also facilitates the proliferation of AM precursors and developing AMs (FIG. 3A and FIG. 3B).

The observation that tissue-resident, long-lived macrophages arise during prenatal development and then self-renew (C. Schulz et al., Science 336, 86-90 (2012)) overturned the long-standing presumption that tissue-resident macrophages are continually repopulated from circulating blood monocytes. This finding prompted new work demonstrating the different ontogeny and function of varied macrophage lineages (C. Schulz et al., Science 336,86-90 (2012); S. Yona et al., Immunity 38, 79-91 (2013); C. Schneider et al., Nat. Immunol. 15, 1026-1037 (2014); E. Gomez Perdigueroet al., Nature 518, 547-551 (2015); M. Kopf et al., Nat. Immunol. 16, 36-44 (2015); E. Mass Science 353, aaf4238 (2016); L. van de Laar et al., Immunity 44, 755-768 (2016); and D. Hashimoto et al., Immunity 38, 792-804 (2013)). AMs represent a unique phagocytic lineage with a limited temporal window for development, occurring in the perinatal period and driven by a "burst" of GM-CSF occurring shortly after birth. The maturation pathway from fetal liver monocyte to mature AM has been well documented in mice (C. Schneider et al., Nat. Immunol. 15, 1026-1037 (2014)), and several key regulators have been identified (X. Yu et al., Immunity 47, 903-912.e4 (2017)). Translation to humans, which requires mapping of ontology and functional phenotypes of the multiple interstitial and AMs in mice to corresponding lineages in humans, will inform the role of each lineage in both lung infection and chronic lung disease (CLD) in preterm infants. One major obstacle to clinical translation has recently been overcome, as markers for clear differentiation of human AMs from interstitial lung macrophages have recently been defined (A.

Bharat et al., Am. J. Respir. Cell Mol. Biol. 54, 147-149 (2016); R. Carr et al., Cochrane Database Syst. Rev. 2003, CD003066 (2003)). The recent characterization of distinct lineages (K. J. Mould et al., Am. J. Respir. Cell Mol. Biol. 57, 294-306 (2017), S. L. Gibbings et al., Am. J. Respir. Cell Mol. Biol. 57, 66-76 (2017)) now enables the re-evaluation of prior links between CLD outcome and lung macrophages; for instance, the macrophages studied in a landmark paper examining alveolarization inhibition by macrophage-specific pro-inflammatory signaling (T. S. Blackwell et al., J. Immunol. 187, 2740-2747 (2011)) were, in retrospect, likely fetal interstitial lung macrophages rather than AMs. The pathogenesis of CLD (including inhibition of airway maturation) might be greatly clarified by additional studies leveraging new knowledge of macrophage lineages and AM development.

Existing clinical data, examined in light of the new murine paradigm, support the consideration of AM maturation as a therapeutic target. First, a similar monocyte-to-AM maturation may occur in human infants (E. Alenghat et al., Pediatrics 74, 221-223 (1984), L. R. Prince et al., PLOS ONE 9, e103059 (2014)). While preterm lungs have been shown to bear monocytes (L. R. Prince et al., PLOS ONE 9, e103059 (2014)), very few, if any, mature AMs are present in the lungs of stillborn infants (E. Alenghat et al., Pediatrics 74, 221-223 (1984), A. Bharat et al., Am. J. Respir. Cell Mol. Biol. 54, 147-149 (2016)), strongly suggesting that AMs are not present in the lungs of infants in utero. In a cohort of live-born infants who died in the early neonatal period, AMs were present in 33 of 46 (72%) infants who died before 48 hours of age but were apparent in the lungs of 50 of 54 (93%) infants who survived longer than 48 hours (E. Alenghat et al., Pediatrics 74, 221-223 (1984)). Thus, the emergence of AMs in the lungs of neonates correlated with time since birth, consistent with the murine model in which AM precursors differentiate to mature AM shortly after birth.

Moreover, the developmentally regulated increase of GM-CSF noted in newborn mice has also been observed in humans (K. Bry et al., Pediatr. Res. 41, 105-109 (1997)). An analysis of GM-CSF concentrations in amniotic fluid revealed gradually increasing GM-CSF concentrations, beginning at 28 weeks of gestation (K. Bry et al., Pediatr. Res. 41, 105-109 (1997)). After birth, tracheal aspirates demonstrated a sharp and significant increase in GM-CSF concentrations in samples between 12 and 48 hours of age, after which concentrations did not change appreciably (K. Bry et al., Pediatr. Res. 41, 105-109 (1997)). This study provides evidence that GM-CSF may also increase at the time of birth in human infants, concurrently with the appearance of mature AMs.

Because AMs are phenotypically and functionally distinct from the interstitial macrophage lineages, delayed or disturbed AM maturation in preterm and term neonates could be pathophysiologically linked to either impaired immunity or increased pro-inflammatory signaling associated with bronchopulmonary dysplasia or CLD. For instance, the analysis of BAL fluid from preterm infants revealed a significant increase in nonclassical, pro-inflammatory CD14+/CD16+ monocyte-macrophages and a decrease in the anticipated mature, anti-inflammatory CD14+/CD36+ macrophages compared to term infants. Furthermore, preterm infants that developed CLD had significantly fewer mature anti-inflammatory CD14+/CD36+ macrophages (AMs) recovered from BAL fluid than did preterm infants who did not develop CLD. Results from this study thus correlate with mouse ontogeny models, in that a higher proportion of immature (monocytic) cells is observed in preterm infants, and suggest that this perturbation is associated with CLD (L. R. Prince et al., PLOS ONE 9, e103059 (2014)).

The present Example supports the concept that the augmentation of AM number and function, if perturbed in preterm infants, could confer translational benefit to the preterm lung, both by protecting against pulmonary infection (a common complication of prematurity) and by promoting surfactant function and metabolism [as reduced AM number impairs surfactant catabolism (A. V. Andreeva et al., Am. J. Physiol. Lung Cell. Mol. Physiol. 293, L259-L271 (2007); J. R. Wright et al., Am. J. Physiol. 268, L772-L780 (1995); and Q. Dong et al. Am. J. Physiol. 274, L97-L105 (1998))]. In the $LPL^{-/-}$ mouse model of deficient AM maturation, intranasal rGM-CSF restored AM numbers and provided durable protection against pneumococcal challenge. Similarly, in preterm rabbits, reduced AM number correlated with increased susceptibility to group B streptococcal (GBS) lung infection (M. P. Sherman et al., J. Infect. Dis. 166, 818-826 (1992)). Specifically, preterm rabbits harbored barely detectable AMs and permitted the proliferation of GBS in the lungs, while term rabbits had 17-fold higher numbers of AMs than preterms and easily cleared a similar pulmonary GBS challenge (M. P. Sherman et al., J. Infect. Dis. 166,818-826 (1992)). An increase in SP-D concentrations in $LPL^{-/-}$ neonatal pups is also shown (FIG. 4A), consistent with reduced surfactant catabolism that would be anticipated with diminished numbers of AMs [FIG. 1B and (M. P. Sherman et al., J. Infect. Dis. 166, 818-826 (1992))]. Exogenous neonatal rGM-CSF therapy reduced SP-D concentrations in PND3 $LPL^{-/-}$ pup lungs concordant with the acceleration in AM maturation, suggesting that the airway administration of GM-CSF to augment AM maturation may promote surfactant homeostasis in preterm neonates.

The present data shows that administering three doses of intranasal GM-CSF to neonatal mice is feasible and was effective in promoting AM maturation and pneumococcal clearance. The airway administration of GM-CSF has not been previously studied in clinical trials of human infants (M. P. Sherman et al., J. Infect. Dis. 166, 818-826 (1992)). One major clinical trial of GM-CSF administered subcutaneous (systemic) GM-CSF to preterm infants within 72 hours of birth, with a primary end point of sepsis-free survival at 14 days of life and with a goal of increasing peripheral neutrophil counts. No survival benefit of systemic GM-CSF was observed in this study nor were any differences in oxygen requirements observed at 28 days from enrollment (M. P. Sherman et al., J. Infect. Dis. 166, 818-826 (1992)). Follow-up evaluations of 2- and 5-year outcomes revealed no differences in neurodevelopmental, growth, or infectious outcomes with systemic GM-CSF administration (N. Marlow et al., Arch. Dis. Child. Fetal Neonatal Ed. 98, F46-F53 (2012), N. Marlow et al., Arch. Dis. Child. Fetal Neonatal Ed. 100, F320-F326 (2015)). It was found that the subcutaneous administration of GM-CSF did not increase AM maturation as did direct airway administration (FIG. 5). It is proposed that direct airway administration results in higher alveolar concentrations of rGM-CSF than does systemic injection, as systemic injection would distribute rGM-CSF throughout all tissues, while direct airway administration would provide a high alveolar concentration before systemic absorption. Further pharmacokinetic studies could define optimal dosing and timing of neonatal rGM-CSF to modify AM development. A meta-analysis revealed a higher response rate and greater improvements in PaO2 in subjects with autoimmune pulmonary alveolar proteinosis treated with inhaled GM-CSF than with subcutaneous GM-CSF (G. Sheng et al., A meta-analyses. Respir. Res. 19, 163 (2018)). Inhaled GM-CSF has recently been used to successfully treat Mycobacterium abscessus infections in two patients with cystic fibrosis (J. P. Scott et al., Eur. Respir. J. 51, 1702127 (2018)). It is further noted that we did not find any evidence of adverse effects of neonatal rGM-CSF airway administration to WT animals, in which AM maturation would be expected to be proceeding normally, as assessed by alveolarization, surfactant protein concentrations, and infectious susceptibility. It is therefore suggested that revisiting GM-CSF therapy in neonates via this alternate route of administration is warranted.

Furthermore, administering rGM-CSF to neonates with perturbed AM development produced a longer-lasting effect (8 to 12 weeks) than prior techniques using GM-CSF to protect against lung infections (K. Steinwede et al., J. Immunol. 187, 5346-5356 (2011)). For instance, adenoviral-mediated expression continuously delivered GM-CSF to the airway and protected mice from pneumococcal pneumonia 14 days later, but the effect of GM-CSF on leukocyte recruitment waned after 28 days of administration (K. Steinwede et al., J. Immunol. 187, 5346-5356 (2011)). The airway administration of GM-CSF also improved clearance of pneumococcus when given to adult mice from 12 hours before 6 hours after infection, but clinical translation of this application was limited by the narrow window of time for effective GM-CSF administration in relation to pneumococcal infection (K. Steinwede et al., J. Immunol. 187, 5346-5356 (2011)). The airway overexpression of GM-CSF driven by a surfactant promoter was also protective in a model of influenza infection, as was the administration of GM-CSF 1 week before infection (F. F. Huang et al., Am. J. Respir. Crit. Care Med. 184, 259-268 (2011)). However, the sustained expression of GM-CSF by either adenoviral or transgenic expression is not clinically translatable, and the effect of GM-CSF administered to adults was not durable. The present approach of administering GM-CSF during the neonatal window of AM development is therefore unique and clinically adaptable. It is noted that the present study did not challenge WT mice with a pneumococcal inoculum anticipated to induce notable mortality, as the intention was to test whether neonatal rGM-CSF therapy of $LPL^{-/-}$ mice rescued susceptibility (FIG. 2A). While the present results conclude that neonatal rGM-CSF therapy did not increase susceptibility of WT animals to lung pneumococcal infection, further studies at higher inocula are required to test whether neonatal rGM-CSF therapy also boosts antipneumococcal immunity in WT mice. Lastly, also supporting the translatability of this approach, GM-CSF has been administered to the airways of a small cohort of adults with refractory acute respiratory distress syndrome, providing benefit in oxygenation and lung compliance compared with control patients (S. Herold et al., Am. J. Respir. Crit. Care Med. 189,609-611 (2014)). The successful use of rGM-CSF to provide sustained protection against bacterial pneumonia in susceptible neonatal mice, without perturbing airway immunity and lung development in the normal host, illuminates how the airway administration of GM-CSF might be used in preterm infants to improve clinical outcomes in this highly vulnerable patient population.

What is claimed is:

1. A method of decreasing susceptibility to a respiratory tract infection in a preterm neonate subject in need thereof, wherein the subject is further in need of improved lung surfactant homeostasis, the method comprising, administering to the subject a composition comprising granulocyte-macrophage colony stimulating factor (GM-CSF) or a functional homologue thereof via pulmonary airway administration.

2. The method of claim 1, wherein the GM-CSF or a functional homologue thereof is administered at birth or shortly thereafter.

3. The method of claim 2, wherein shortly after birth is within about 1 minute, within about 2 minutes, within about 3 minutes, within about 4 minutes, within about 5 minutes, within about 10 minutes, within about 15 minutes, within about 20 minutes, within about 25 minutes, within about 30 minutes, within about 35 minutes, within about 40 minutes, within about 45 minutes, within about 50 minutes, within about 55 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours after birth.

4. The method of claim 1, wherein the GM-CSF or a functional homologue thereof is administered by intratracheal, intrabronchial or intraalveolar administration.

5. The method of claim 1, wherein the subject is administered a nebulized aerosol, nebulized solution or inhaled powder form of GM-CSF or a functional homologue thereof.

6. The method of claim 1, wherein the GM-CSF or functional homologue thereof is administered at birth and at least one time shortly thereafter.

7. The method of claim 1, wherein the susceptibility of infection in the subject is reduced relative to a subject with pulmonary dysfunction resulting from impaired AM development and has not been treated with GM-CSF or a functional homologue thereof.

8. The method of claim 1, wherein the respiratory tract infection is bacterial pneumonia.

9. A method of treating a preterm neonate subject having or suspected of having pulmonary dysfunction, wherein the subject is in need of improved lung surfactant homeostasis, the method comprising, administering to the subject a composition comprising granulocyte-macrophage colony stimulating factor (GM-CSF) or a functional homologue thereof via pulmonary airway administration.

10. The method of claim 9, wherein the GM-CSF or a functional homologue thereof is administered at birth or shortly thereafter.

11. The method of claim 10, wherein shortly after birth is within about 1 minute, within about 2 minutes, within about 3 minutes, within about 4 minutes, within about 5 minutes, within about 10 minutes, within about 15 minutes, within about 20 minutes, within about 25 minutes, within about 30 minutes, within about 35 minutes, within about 40 minutes, within about 45 minutes, within about 50 minutes, within about 55 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours after birth.

12. The method of claim 9, wherein the GM-CSF or a functional homologue thereof is administered by intratracheal, intrabronchial or intraalveolar administration.

13. The method of claim 9, wherein the subject is administered a nebulized aerosol, nebulized solution or inhaled powder form of GM-CSF or a functional homologue thereof.

14. The method of claim 9, wherein the GM-CSF or functional homologue thereof is administered at birth and at least one time shortly thereafter.

15. The method of claim 9, wherein administration of GM-CSF or a functional homologue thereof results in increased alveolar macrophage or alveolar macrophage precursor proliferation.

16. The method of claim 9, wherein administration of GM-CSF or a functional homologue thereof results in improved lung surfactant homeostasis.

17. The method of claim 16, further comprising measuring the levels of one or more of surfactant protein-D and surfactant protein-A to determine improved lung surfactant homeostasis.

18. The method of claim 17, wherein the level of surfactant protein-D is reduced relative to a subject with pulmonary dysfunction resulting from impaired alveolar macrophage (AM) development.

* * * * *